(12) United States Patent
Jarstad et al.

(10) Patent No.: US 9,238,810 B2
(45) Date of Patent: Jan. 19, 2016

(54) POLYPEPTIDE

(75) Inventors: Anders Erik Jarstad, Uppsala (SE); Thomas Bergman, Knivsta (SE); Lars B Abrahmsén, Bromma (SE); Christofer Lendel, Farsta (SE); Karin Nord, Älvsjö (SE)

(73) Assignee: AFFIBODY AB, Solna (SE)

( * ) Notice: Subject to any disclaimer, the term of this patent is extended or adjusted under 35 U.S.C. 154(b) by 1139 days.

(21) Appl. No.: 12/996,260

(22) PCT Filed: Sep. 24, 2008

(86) PCT No.: PCT/EP2008/062754
§ 371 (c)(1),
(2), (4) Date: Feb. 23, 2011

(87) PCT Pub. No.: WO2009/146755
PCT Pub. Date: Dec. 10, 2009

(65) Prior Publication Data
US 2011/0144302 A1    Jun. 16, 2011

Related U.S. Application Data

(60) Provisional application No. 61/130,992, filed on Jun. 5, 2008.

(51) Int. Cl.
| | |
|---|---|
| *C07K 14/31* | (2006.01) |
| *C07K 14/00* | (2006.01) |
| *C07K 17/02* | (2006.01) |
| *C12N 15/10* | (2006.01) |

(52) U.S. Cl.
CPC ............ *C12N 15/1086* (2013.01); *C07K 14/00* (2013.01); *C07K 14/31* (2013.01); *C07K 17/02* (2013.01); *C07K 2317/52* (2013.01)

(58) Field of Classification Search
None
See application file for complete search history.

(56) References Cited

U.S. PATENT DOCUMENTS

| 8,674,073 B2 * | 3/2014 | Majima et al. ................ 530/350 |
| 2010/0168395 A1 * | 7/2010 | Sato .......................... 530/387.3 |

FOREIGN PATENT DOCUMENTS

| EP | 1 992 692 A1 | 11/2008 |
| WO | 01/05808 A2 | 1/2001 |
| WO | 03/080655 A1 | 10/2003 |
| WO | 2007/065635 A1 | 6/2007 |
| WO | 2007/097361 A1 | 8/2007 |
| WO | WO 2007/097361 * | 8/2007 |

OTHER PUBLICATIONS

Caroline Gronwall, et al; "Selection and characterizatio of Affibody ligands binding to Alzheimer amyloid β peptides", Journal of Biotechnology, Elseview Science Publishers, Amsterdam, NL, vol. 128, No. 1, Dec. 23, 2006, pp. 162-183, XP00573469, ISSN: 0168-1656.
International Search Report: PCT/EP2008/062754 (Mar. 18, 2009).

* cited by examiner

*Primary Examiner* — Xiaozhen Xie
(74) *Attorney, Agent, or Firm* — Cantor Colburn LLP

(57) ABSTRACT

The invention provides an immunoglobulin G Fc region binding polypeptide, which polypeptide comprises an immunoglobulin G Fc region binding motif, BM, consisting of an amino acid sequence selected from: i) $EQQX_4AFYEILHLPNLTEX_{18}QX_{20}X_{21}AFIX_{25}X_{26}LRX_{29}$, (SEQ ID NO:12) and ii) an amino acid sequence which has at least 85% identity to the sequence defined in i). Also provided are methods of isolation or production of IgG Fc-containing molecules.

36 Claims, 14 Drawing Sheets

| Polypeptide | Amino acid sequence | SEQ ID NO: |
|---|---|---|
| BM02674 | EQQNAFYEIL HLPNLTEDQR HAFIGTLRA | 1 |
| BM02726 | EQQHAFYEIL HLPNLTEDQR QAFIASLRK | 2 |
| BM02742 | EQQHAFYEIL HLPNLTEGQK HAFIRALRG | 3 |
| | FWKEQQNAFY EILHLPNLTE DQRHAFIGTL RADPSQSARL LAQAKKLDDA Q | 4 |
| | FWKEQQHAFY EILHLPNLTE DQRQAFIASL RKDPSQSARL LAGAKKLDDA Q | 5 |
| | FWKEQQHAFY EILHLPNLTE GQKHAFIRAL RGDPSQSARL LARAKKLDDA Q | 6 |
| Z02674 | VDAKFWKEQQ NAFYEILHLP NLTEDQRHAF IGTLRADPSQ SARLLAQAKK LDDAQAPK | 7 |
| Z02726 | VDAKFWKEQQ HAFYEILHLP NLTEDQRQAF IASLRKDPSQ SARLLAGAKK LDDAQAPK | 8 |
| Z02742 | VDAKFWKEQQ HAFYEILHLP NLTEGQKHAF IRALRGDPSQ SARLLARAKK LDDAQAPK | 9 |
| Z00000 | VDNKFNKEQQ NAFYEILHLP NLNEEQRNAF IQSLKDDPSQ SANLLAEAKK LNDAQAPK | 10 |
| Z01730 | VDNKFNKEQQ SAFYEILHLP NLNEGQEHAF INSLRDDPSQ SANLLAEAKK LNDAQAPK | 11 |

1
POLYPEPTIDE

CROSS REFERENCE TO RELATED APPLICATIONS

This application is a 371 National Stage of PCT Application No.: PCT/EP2008/062754 filed Sep. 24, 2008 which claims priority to U.S. Provisional Application No. 61/130,992 filed Jun. 5, 2008, both of which are incorporated herewith in their entirety.

FIELD OF THE INVENTION

This invention relates to a polypeptide which binds to immunoglobulin G Fc (IgG Fc). The polypeptide has industrial application for example in affinity separation and/or purification in the production of antibodies and/or Fc fusion proteins.

BACKGROUND

In the industrial production of monoclonal antibodies and Fc fusion proteins, purification is frequently carried out using affinity chromatography. Protein A from *Staphylococcus aureus* has long been used as affinity ligand in such applications, due to the native affinity of Protein A for the Fc portion of IgG. Protein A in its entirety, as well as the individual Fc-binding domains thereof, have subsequently served as starting points for the rational design of engineered affinity ligands with improved properties. Despite the comparable success of currently used IgG Fc affinity ligands, there is a continued need for improvement. The continued provision of agents having an affinity for IgG Fc that is comparable with, or higher than, that exhibited by Protein A remains a matter of substantial interest. For example, Protein A affinity chromatography typically uses low pH conditions, which may lead to loss of yield due to the sensitivity of several antibodies and Fc fusion proteins to low pH conditions. The provision of new IgG Fc-binding agents that allow elution at a higher pH as compared to Protein A during affinity chromatography would therefore be beneficial.

It is an object of the invention to provide new IgG Fc-binding agents, that could for example be used in the production of antibodies or Fc fusion proteins, e.g. for affinity separation and/or purification.

SUMMARY OF THE INVENTION

According to one aspect thereof, the invention provides an immunoglobulin G Fc (IgG Fc) binding polypeptide, comprising an IgG Fc-binding motif, BM, which motif consists of an amino acid sequence selected from:

```
                                           (SEQ ID NO: 12)
i) EQQX₄AFYEIL HLPNLTEX₁₈QX₂₀ X₂₁AFIX₂₅X₂₆LRX₂₉,
``` wherein, independently of each other,
$X_4$ is selected from H and N;
$X_{18}$ is selected from D and G;
$X_{20}$ is selected from R and K;
$X_{21}$ is selected from H and Q;
$X_{25}$ is selected from R, A and G;
$X_{26}$ is selected from A, S and T; and
$X_{29}$ is selected from G, K and A;
and 2
ii) an amino acid sequence which has at least 85% identity to the sequence defined in i).

The above definition of a class of sequence related, IgG Fc-binding polypeptides according to the invention is based on an analysis of a number of random polypeptide variants of a parent scaffold, that were selected from a combinatorial protein library for their interaction with IgG Fc in phage display selection experiments (Examples 1 and 2). The identified IgG Fc-binding motif, or "BM", corresponds to the target binding region of the parent scaffold, which region constitutes two alpha helices within a three-helical bundle protein domain. In the parent scaffold, the varied amino acid residues of the two BM helices include amino acid residues that participate in the binding surface for interaction with Fc. In the present invention, the random variation of surface residues and the subsequent selection of variants have modified the original Fc interaction capacity.

As the skilled person will realize, the function of any polypeptide, such as the IgG Fc-binding capacity of the polypeptides according to the invention, is dependent on the tertiary structure of the polypeptide. It is therefore possible to make minor changes to the sequence of amino acids in a polypeptide without affecting the function thereof. Thus, the invention encompasses modified variants of the BM of i), which are such that the resulting sequence is at least 85% identical to a sequence belonging to the class defined by i). For example, it is possible that an amino acid residue belonging to a certain functional grouping of amino acid residues (e.g. hydrophobic, hydrophilic, polar etc) could be exchanged for another amino acid residue from the same functional group.

In one embodiment of the polypeptide according to the invention, $X_4$ is H.
In one embodiment of the polypeptide according to the invention, $X_{18}$ is G.
In one embodiment of the polypeptide according to the invention, $X_{20}$ is K.
In one embodiment of the polypeptide according to the invention, $X_{21}$ is H.
In one embodiment of the polypeptide according to the invention, $X_{25}$ is R.
In one embodiment of the polypeptide according to the invention, $X_{26}$ is A.
In one embodiment of the polypeptide according to the invention, $X_{29}$ is G.

As described in detail in the experimental section to follow, the selection of IgG Fc-binding variants has led to the identification of individual IgG Fc-binding motif (BM) sequences. These sequences constitute individual embodiments of the BM sequence i) in the definition of IgG Fc-binding polypeptides according to this aspect of the present invention. The sequences of individual IgG Fc-binding motifs are presented in FIG. 1 and as SEQ ID NO:1-3 (FIG. 1). In embodiments of this aspect of the invention, the BM sequence i) may in particular be SEQ ID NO:1.

In embodiments of the present invention, the BM may form part of a three-helix bundle protein domain. For example, the BM may essentially constitute or form part of two alpha helices with an interconnecting loop, within said three-helix bundle protein domain.

In particular embodiments of the invention, such a three-helix bundle protein domain is selected from domains of bacterial receptor proteins. Non-limiting examples of such domains are the five different three-helical domains of protein A from *Staphylococcus aureus*, and derivatives thereof. Thus, an IgG Fc-binding polypeptide according to the invention may comprise an amino acid sequence selected from:

ADNNFNK-[BM]-DPSQSANLLSEAKKLNESQAPK (SEQ ID NO: 13)
(BM within domain A of staphylococcal protein A);

ADNKFNK-[BM]-DPSQSANLLAEAKKLNDAQAPK (SEQ ID NO: 14)
(BM within domain B of staphylococcal protein A);

ADNKFNK-[BM]-DPSVSKEILAEAKKLNDAQAPK (SEQ ID NO: 15)
(BM within domain C of staphylococcal protein A);

ADAQQNNFNK-[BM]-DPSQSTNVLGEAKKLNESQAPK (SEQ ID NO: 16)
(BM within domain D of staphylococcal protein A);

AQHDE-[BM]-DPSQSANVLGEAQKLNDSQAPK (SEQ ID NO: 17)
(BM within domain E of staphylococcal protein A);
and VDNKFNK-[BM]-DPSQSANLLAEAKKLNDAQAPK (SEQ ID NO: 18)
(BM within the protein Z derivative of domain B of staphylococcal protein A);

wherein [BM] is an IgG Fc-binding motif as defined above.

In alternative embodiments of the present invention, wherein the BM again essentially constitutes or forms part of two alpha helices with an interconnecting loop, within said three-helix bundle protein domain, the IgG Fc-binding polypeptide comprises the amino acid sequence:

FWK-[BM]-DPSQSARLLA $X_a$ AKKLDDAQ, (SEQ ID NO: 19)

wherein [BM] is an IgG Fc-binding motif as defined above, and $X_a$ is selected from R, G and Q.

For example, the IgG Fc-binding polypeptide may comprise the amino acid sequence:

VDAKFWK-[BM]-DPSQSARLLAX$_a$AKKLDDAQAPK, (SEQ ID NO: 20)

wherein [BM] is an IgG Fc-binding motif as defined above, and $X_a$ is selected from R, G and Q.

In some examples of these embodiments, $X_a$ is R.

The IgG Fc-binding polypeptide may for example comprise an amino acid sequence selected from SEQ ID NO:4-6, such as SEQ ID NO:4 (FIG. 1).

According to another alternative aspect thereof, the invention provides an IgG Fc-binding polypeptide, whose amino acid sequence comprises a sequence which fulfils one definition selected from the following: iii) it is selected from SEQ ID NO:7-9, and iv) it is an amino acid sequence having 85% or greater identity to a sequence selected from SEQ ID NO:7-9 (FIG. 1). In embodiments of this aspect of the invention, the IgG Fc-binding polypeptide may in particular comprise SEQ ID NO:7, or a sequence having 85% or greater identity thereto.

When reference is made herein to the degree of identity between the amino acid sequences of different polypeptides, the lower limit of 85 identity to a sequence disclosed herein is given. In some embodiments, the inventive polypeptide may have a sequence which is at least 86%, at least 87%, at least 88%, at least 89%, at least 90%, at least 91%, at least 92%, at least 93%, at least 94%, at least 95%, at least 96%, at least 97%, at least 98% or at least 99% identical to the sequence described herein. The comparison may be performed over a window corresponding to the shortest of the sequences being compared, or over a window corresponding to an IgG Fc-binding motif in at least one of the sequences being compared.

An IgG Fc-binding polypeptide according to any aspect of the invention may bind to IgG Fc such that the $K_D$ value of the interaction is at most $1 \times 10^{-6}$ M, for example at most $1 \times 10^{-7}$ M, such as at most $5 \times 10^{-8}$ M.

The polypeptide is advantageous in that it binds well to an IgG Fc. In particular, the polypeptide may be capable of binding to the Fc portion of a human IgG molecule. In some embodiments of the invention, the polypeptide is capable of binding to classes 1, 2 and 4 of human IgG, but not to class 3. In some embodiments, the polypeptide is capable of binding to the interface between the CH2 and CH3 domains of IgG Fc. In some embodiments, the polypeptide is capable of binding to an area on the Fc molecular surface made up by the Fc amino acid residues T250-S254, T256, L309-L312, L314, D315, E430 and L432-Y436 (numbering according to Deisenhofer, Biochemistry (1981) 20(9):2361-70).

The skilled addressee will appreciate that various modifications and/or additions can be made to a polypeptide according to the invention in order to tailor the polypeptide to a specific application without departing from the scope of the present invention. These modifications and additions are described in more detail below and may include additional amino acids in the same polypeptide chain, or labels and/or therapeutic agents that may be chemically conjugated or otherwise bound to the polypeptide of the invention.

Furthermore, the invention also encompasses fragments of IgG Fc-binding polypeptides according to the invention that retain IgG Fc-binding. The possibility of creating fragments of a wild-type Staphylococcus aureus protein A domain with retained binding specificity was shown by Braisted A C et al in Proc Natl Acad Sci USA 93:5688-5692 (1996). In the experiments described in that paper, using a structure-based design and phage display methods, the binding domain of a three-helix bundle of 59 residues was reduced to a resulting two-helix derivative of 33 residues. This was achieved by stepwise selection of random mutations from different regions, which caused the stability and binding affinity to be iteratively improved. Following the same reasoning, with the polypeptides of the present invention, the skilled addressee will be able to obtain a "minimized" IgG Fc-binding polypeptide with the same binding properties as that of the "parent" IgG Fc-binding polypeptide. Thus, a polypeptide constituting a fragment of a polypeptide according to the invention is within the scope of the invention.

The terms "IgG Fc-binding" and "binding affinity for IgG Fc" as used in this specification refers to a property of a polypeptide which may be tested for example by the use of surface plasmon resonance technology, such as in a Biacore instrument (GE Healthcare). For example as described in the examples below, IgG Fc-binding affinity may be tested in an experiment in which IgG Fc, or a fragment of IgG Fc, is immobilized on a sensor chip of the instrument, and the sample containing the polypeptide to be tested is passed over the chip. Alternatively, the polypeptide to be tested is immobilized on a sensor chip of the instrument, and a sample containing IgG Fc, or fragment thereof, is passed over the chip. The skilled person may then interpret the results obtained by such experiments to establish at least a qualitative measure of the binding affinity of the polypeptide for IgG Fc. If a quantitative measure is desired, for example to determine a $K_D$ value for the interaction, surface plasmon resonance methods may also be used. Binding values may for example be defined in a Biacore 2000 instrument (GE Healthcare). IgG Fc is immobilized on a sensor chip of the measurement, and samples of the polypeptide whose affinity is to be determined are prepared by serial dilution and injected in random order. $K_D$ values may then be calculated from the results using for example the 1:1 Langmuir binding model of the BIAevaluation 4.1 software provided by the instrument manufacturer.

Where amino acid substitutions are introduced, these should not affect the basic structure of the polypeptide. For example, the overall folding of the C$\alpha$ backbone of the polypeptide can be essentially the same as that of a domain of protein A, i.e. having the same elements of secondary structure in the same order. Thus, polypeptides having this basic structure will have similar CD spectra to the wild-type protein A domain. The skilled addressee is aware of other parameters that may be relevant. The requirement of conserving the basic structure, places restrictions on which positions of the amino acid sequence may be subject to substitution. For example, it is preferred that amino acid residues located on the surface of the polypeptide are substituted, whereas amino acid residues buried within the core of the polypeptide "three-helix bundle" should be kept constant in order to preserve the structural properties of the molecule. The same reasoning applies to fragments of polypeptides of the invention.

The invention also covers polypeptides in which the IgG Fc-binding polypeptide described above is present as an IgG Fc-binding domain to which additional amino acid residues have been added at either terminal. These additional amino acid residues may play a role in the binding of IgG Fc by the polypeptide, but may equally well serve other purposes, related for example to one or more of the production, purification, stabilization in vivo and/or in vitro, coupling or detection of the polypeptide. Such additional amino acid residues may comprise one or more amino acid residues added for the purpose of chemical coupling. One example of this is the addition of a cysteine residue N-terminally or C-terminally with respect to the binding motif, e.g. close to or at the N or C terminus. Such additional amino acid residues may also provide a "tag" for purification or detection of the polypeptide such as a $His_6$ tag or a "myc" (c-myc) tag or a "FLAG" tag for interaction with antibodies specific to the tag.

The present invention also covers IgG Fc-binding polypeptides in which an IgG Fc-binding polypeptide as described above is present as an IgG Fc-binding domain to which additional peptides or proteins or other functional groups are coupled N- or C-terminally or to any other residues (specifically or non-specifically) by means of chemical conjugation (using known organic chemistry methods).

The "additional amino acid residues" discussed above may also provide one or more polypeptide domains with any desired function, such as the same binding function as the first, IgG Fc-binding domain, or another binding function, or an enzymatic function, toxic function (e.g. an immunotoxin), or a fluorescent signaling function, or combinations thereof.

The polypeptide of the invention may be in monomeric or multimeric forms. Multimeric forms of the polypeptide may be advantageous in that they may have enhanced binding properties. Preferred multimeric forms include dimeric, trimeric and tetrameric forms. Multimeric forms of the polypeptides may comprise a suitable number of polypeptides of the invention. These polypeptides essentially form domains within the multimer. These domains may all have the same amino acid sequence, but alternatively, they may have different amino acid sequences. The polypeptides may be joined by covalent coupling using known organic chemistry methods, or expressed as one or more fusion polypeptides in a system for recombinant expression of polypeptides, or joined in any other fashion, either directly or via a linker, for example an amino acid linker.

Additionally, fusion polypeptides, in which the IgG Fc-binding polypeptide of the invention provides a first domain or moiety, and second or further moieties have other functions than binding IgG Fc are also contemplated and within the scope of the present invention. The second or further moieties of such a fusion polypeptide may comprise a binding domain with an affinity for another target molecule than IgG Fc. Such a binding domain may be another, similar polypeptide binder. For example, the polypeptide binder may be a variant of protein Z derived from domain B of protein A. This makes it possible to create multi-specific reagents that may be used in several types of applications such as medicine, veterinary medicine, diagnosis, separation, and imaging. The preparation of such multi-specific fusion polypeptides may be performed using methods well known in the art of molecular biology.

In other embodiments of the invention, the second or further moieties may comprise an unrelated, naturally occurring or recombinant protein (or a fragment thereof which retains the binding or other ability of the naturally-occurring or recombinant protein) having a binding affinity for a target. For example, an IgG Fc-binding polypeptide in accordance with the invention may be joined to an albumin-binding domain, such as the albumin binding domain GA3 of protein G from *Streptococcus* strain G148 ("ABD"), or any other polypeptide with affinity for a serum protein.

The IgG Fc-binding polypeptides of the present invention may be provided in the form of other fusion polypeptides. For example the IgG Fc-binding polypeptide, or fragment thereof, may be covalently coupled to a second or further moiety or moieties, which in addition to, or instead of target binding, exhibit other functions. One example would be a fusion between one or more IgG Fc-binding polypeptides and an enzymatically active polypeptide serving as a reporter or effector moiety. Examples of reporter enzymes, which may be coupled to the IgG Fc-binding polypeptide to form a fusion protein, are well-known to the skilled person and include enzymes such as β-galactosidase, alkaline phosphatase, horseradish peroxidase, carboxypeptidase. Other options for the second and further moiety or moieties of a fusion polypeptide according to the invention include fluorescent polypeptides, such as green fluorescent protein, red fluorescent protein, luciferase and variants thereof.

A polypeptide according to the invention may be useful in any method which relies on affinity for IgG Fc of a reagent. Thus, the polypeptide may be used as a detection reagent, a capture reagent or a separation reagent in such methods. In particular, the polypeptide exhibits several characteristics which make it useful as an affinity reagent in affinity chromatography, wherein the goal is to separate, purify and/or produce antibodies or Fc fusion proteins from a heterogeneous mixture. The polypeptide can be bound to a matrix and e.g. used for the purification of IgG Fc-containing therapeutic compounds in industrial production. Due to properties such as a high target affinity, a high stability both in acidic and basic environments and a high selectivity for the IgG Fc fragment over the IgG Fab fragment, the IgG Fc-binding polypeptide according to the invention is thought to present a very attractive affinity reagent.

Thus, another aspect of the present invention is a method of isolating molecules comprising IgG Fc from a sample, which method comprises the steps:

(i) providing a sample containing molecules comprising IgG Fc;

(ii) contacting the sample with an IgG Fc-binding polypeptide as described herein, whereby said molecules comprising IgG Fc bind to the polypeptide;

(iii) isolating bound molecules comprising IgG Fc from the sample.

In the inventive isolation method, the sample may be derived from a culture of prokaryotic or eukaryotic, such as mammalian or plant, cells expressing molecules comprising IgG Fc, or from expression of such molecules in an alternative expression system, for example a vesicular system. Alternatively, the sample may be derived from transgenic expression in a host, such as a plant or mammalian host.

In some embodiments, said molecules comprising IgG Fc are IgG molecules or fragments thereof. For example, they can be human IgG molecules or fragments thereof. In some embodiments, said molecules comprising IgG Fc are monoclonal IgG antibodies. In particular, such monoclonal IgG antibodies may be human monoclonal IgG antibodies. For example, they are human monoclonal IgG antibodies from class 1, 2 and/or 4.

In other embodiments, said molecules comprising IgG Fc are Fc fusion proteins. The Fc domain in such a fusion protein may thus, advantageously, be used as an "affinity handle" in the isolation of the fusion protein. A large variety of Fc fusion proteins have been created. For example, Fc fusion proteins having therapeutic applications include etanercept, which is a fusion between soluble TNF-α receptor and Fc, and VEGF Trap, which is a fusion between VEGF receptor domains and Fc (Holash et al, Proc Natl Acad Sci USA (2002) 99(17): 11393-11398). While these two are illustrative examples of great interest, the listing of them is non-limiting, and it is in principle possible to fuse an Fc domain to any desired protein in order to modify its properties and facilitate affinity purification thereof using the inventive IgG Fc-binding polypeptide described herein as affinity ligand.

Yet another aspect of the present invention concerns a method of producing molecules comprising IgG Fc, which method comprises the steps:

(i) expressing desired molecules comprising IgG Fc;
(ii) obtaining a sample of molecules comprising IgG Fc from said expression;
(iii) contacting the sample with an IgG Fc-binding polypeptide as described herein, whereby molecules comprising IgG Fc bind to the polypeptide;
(iv) isolating bound molecules comprising IgG Fc from the sample, and
(v) recovering bound molecules comprising IgG Fc through elution thereof from the IgG Fc-binding polypeptide.

Expression step (i) may be performed using any known expression system, for example recombinant expression in prokaryotic or eukaryotic, such as mammalian or plant, cells, or in a vesicular system. The sample may also be derived from transgenic expression in a host, such as a plant or mammalian host.

In some embodiments, said molecules comprising IgG Fc are IgG molecules or fragments thereof. For example, they can be human IgG molecules or fragments thereof. In some embodiments, said molecules comprising IgG Fc are monoclonal IgG antibodies. In particular, such monoclonal IgG antibodies may be human monoclonal IgG antibodies. For example, they are human monoclonal IgG antibodies from class 1, 2 and/or 4.

In other embodiments, said molecules comprising IgG Fc are Fc fusion proteins.

In some embodiments of the inventive methods of isolating and producing, the IgG Fc-binding polypeptide is immobilized on a chromatography medium. In general, methods that employ the polypeptides in accordance with the invention in vitro may be performed in different formats, such as on filters or membranes, microtitre plates, in protein arrays, on biosensor surfaces, on beads, in flow cytometry, on tissue sections, and so on. In a specific aspect, the invention provides an affinity chromatography medium, which has an IgG Fc-binding polypeptide as described herein immobilized thereon. Such a medium may be based on any known chromatography material as a matrix, and coupling of the polypeptide to the matrix may be performed using any one of several known procedures.

The numbering of amino acid residues and any use of the term "position" in the sequence of the polypeptide according to the invention is relative. In a polypeptide in accordance with the invention which has as many amino acid residues as a specifically disclosed polypeptide, i.e. those described above, the positions of amino acids in the polypeptide correspond exactly to those in the disclosed polypeptides. In a situation where there is, for example, an N terminal extension compared to the disclosed polypeptides, those amino acid residues in the extended peptide that correspond to those of the non-extended peptide have the same position numbers. For example, if there is a six amino acid residue extension on the extended polypeptide, then amino acid number seven of that modified polypeptide, counting from the N terminus, corresponds to the amino acid in position number one of the disclosed polypeptide.

With regard to the description above of fusion polypeptides and proteins incorporating an IgG Fc-binding polypeptide of the invention, it should be noted that the designation of first, second and further moieties is made for the purposes of clarity to distinguish between the IgG Fc-binding moiety or moieties on the one hand, and moieties exhibiting other functions on the other hand. These designations are not intended to refer to the actual order of the different domains in the polypeptide chain of the fusion protein or polypeptide. Thus, for example, a first moiety may appear at the N-terminal end, in the middle, or at the C-terminal end of the fusion protein or polypeptide.

The invention is further illustrated by the following non-limiting examples.

BRIEF DESCRIPTION OF THE FIGURES

FIG. 1 is a listing of the amino acid sequences of examples of IgG Fc-binding motifs comprised in IgG Fc-binding polypeptides of the invention (SEQ ID NO:1-3), examples of IgG Fc-binding polypeptides according to the invention (SEQ ID NO:4-9), the protein Z derivative of domain B of *Staphylococcus aureus* protein A (SEQ ID NO:10), and the Z variant Z01730 previously obtained by phage display selection from a combinatorial protein library (SEQ ID NO:11).

FIG. 2B: Z02726 and FIG. 2C: Z02742. Z02829 is a derivative of Z02674 containing two substitutions at the beginning of the protein (A8N and W11N with respect to the sequence of the entire expressed molecule, i.e. A3N and W6N with respect to SEQ ID NO:7). Thus, the IgG Fc-binding motif of Z02829 is the same as that of Z02674.

EXAMPLE 1

Figure 2A:
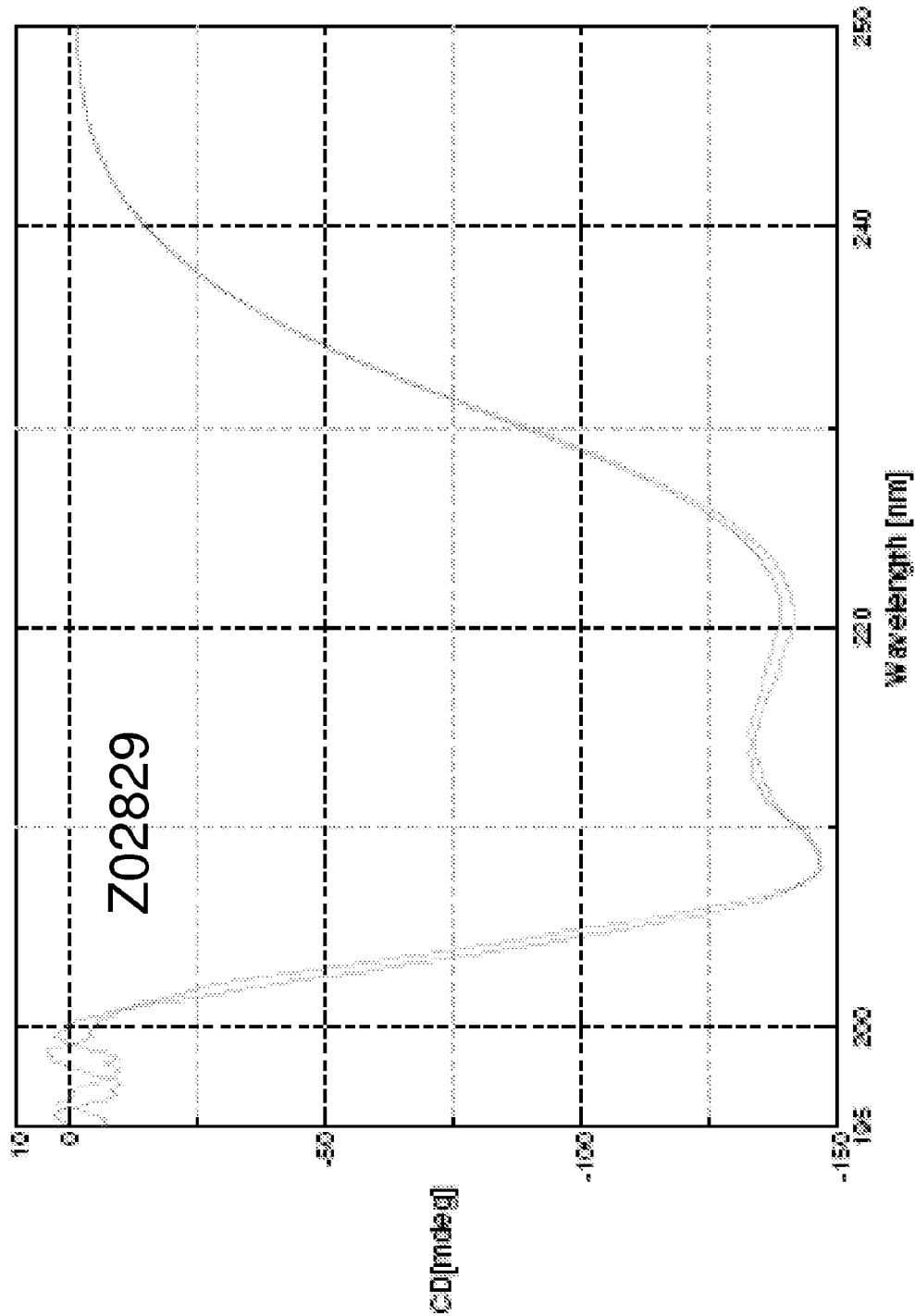
FIGS. 2A, 2B, and 2C show overlay of CD spectra taken at 195-250 nm before and after variable temperature measurement (VTM) involving heating at 90° C. for FIG. 2A: Z02829.

Selection and Initial Characterization of IgG Fc-Binding Polypeptides

In this Example, a Z variant library denoted ZLib2007-IgG, created following an initial selection of IgG binding Z variants from the library ZLib2002 and evaluation of results, was used for selection of IgG Fc-binding polypeptides according to the invention. Details of library construction and selection procedures were generally as described in Grönwall et al, J Biotechnol 128:162-183, 2007. Four different phage display selections from ZLib2007-IgG were made against various IgG and IgG-like molecules. Clones were sequenced, the sequences analyzed by clustering and the amino acid sequence of each clone compared to the distribution of variable amino acids among all selected clones and the distribution in the library design. IgG Fc-binding molecules were chosen for further characterization after four selection rounds, whereupon a fifth round was carried out with more stringent washing conditions, elution at a higher pH and with a higher temperature during selection. Additional IgG Fc-binding molecules derived from selection round 5 were selected for further characterization.

Materials and Methods
Selection

Five selection rounds were performed in each one of four selection setups, and new phage stocks were prepared between each round. Target protein was alternated between selection rounds in some selection setups. Targets used were human immunoglobulin G2κ (IgG2κ) from myeloma serum (Meridian Life Science, cat. no. A50184H), human immunoglobulin G3λ (IgG3λ) from myeloma serum (Meridian Life Science, cat. no. A50186H), human immunoglobulin G4λ (IgG4λ) from myeloma serum (Meridian Life Science, cat. no. A50947H), etanercept (trade name Enbrel®; Apoteket cat. no. 566661, producer Wyeth, lot 21032), biotinylated human immunoglobulin G, Fc fragment (IgG-Fc) (Jackson Immunoresearch, cat. no. 009-060-008, lot 66321), and biotinylated human immunoglobulin G1κ (IgG1κ) (Ancell, cat. no. 295-030, lot 141605). An overview of target proteins in each round of each selection setup is presented in Table 1. The selections were performed against biotinylated target protein in liquid phase for selection against IgG variants, or against target immobilized on a solid phase in the form of the surface of an immunotube for selection against etanercept.

TABLE 1

| | | Selection setups | | | | |
|---|---|---|---|---|---|---|
| Setup | Selection round | Target | Concentration | No. of washes | Time/wash (min) | Elution pH |
| IgG_22-Sel1 | 1 | Poly-IgG-Fc | 100 nM | 2 | 0 | 3.5 |
| | 2 | Etanercept | 6 μg/ml | 2 | 0 | 3.5 |
| | 3 | Poly-IgG-Fc | 20 nM | 4 | 1 | 3.5 |
| | 4 | Etanercept | 3 μg/ml | 5 | 2 | 3.5 |
| | 5 | Poly-IgG-Fc | 20 nM | 9 | 5 | 3.8 |
| IgG_21-Sel1 | 1 | Poly-IgG1&2&4 | 33 + 33 + 33 nM | 2 | 0 | 3.5 |
| | 2 | Poly-IgG1&2&4 | 17 + 17 + 17 nM | 2 | 0 | 3.5 |
| | 3 | Poly-IgG1&2&4 | 7 + 7 + 7 nM | 4 | 1 | 3.5 |
| | 4 | Poly-IgG1&2&4 | 7 + 7 + 7 nM | 5 | 2 | 3.5 |
| | 5 | Poly-IgG1&2&4 | 7 + 7 + 7 nM | 9 | 5 | 3.8/4.5 |
| IgG_23-Sel1 | 1 | Poly-IgG1 | 100 nM | 2 | 0 | 2.2 |
| | 2 | Poly-IgG4 | 50 nM | 2 | 0 | 2.2 |
| | 3 | Poly-IgG2 | 20 nM | 5 | 2 | 2.2 |
| | 4 | Poly-IgG2 | 20 nM | 7 | 3 | 2.2 |
| | 5 | Poly-IgG1 | 20 nM | 13 | 7 | 3.8 |
| IgG_21-Sel2 | 1 | Poly-IgG1&2&4 | 20 + 20 + 20 nM | 2 | 0 | 2.2 |
| | 2 | Poly-IgG1&2&4 | 8 + 8 + 8 nM | 2 | 0 | 2.2 |
| | 3 | Poly-IgG1&2&4 | 4 + 4 + 4 nM | 4 | 1 | 2.2 |
| | 4 | Poly-IgG1&2&4 | 2 + 2 + 2 nM | 5 | 2 | 2.2 |
| | 5 | Poly-IgG1&2&4 | 1 + 1 + 1 nM | 9 | 5 | 3.8 |

Warm conditions for selection (37° C.) and wash (37-45° C.) were used in round 5 in all setups.

Phage library stock was PEG/NaCl precipitated twice and dissolved in 1 ml selection buffer (PBS: 2.68 mM KCl, 1.47 mM $KH_2PO_4$, 137 mM NaCl, 8.1 mM $Na_2HPO_4$, pH 7.4; supplemented with 0.1% Tween20 (Acros Organics cat. no. 2333 62500) and 0.1% gelatine (Prolabo, cat. no. 24 360.233)).

Liquid Phase Selection:

Phages were pre-incubated with streptavidin coated beads (Dynabeads® M-280; Dynal cat. no. 112.06) for 1 hour at room temperature. Pre-clearing against Fab was made in a Maxisorp immunotube (Nunc, cat. no. 444202) coated with Fab. All tubes and beads used in the selection procedure were pre-blocked in selection buffer. Phages were incubated with biotinylated target under agitation for up to 3 hours. Then, the phages were transferred to pre-blocked streptavidin beads and incubated for 15 min with agitation, and the beads were washed in selection buffer according to Table 1.

Solid Phase Selection:

Target protein was immobilized onto immunotubes. Phages were pre-incubated in an immunotube coated with Fab. All tubes, including tubes coated with target, were blocked in selection buffer prior to selection. Phages were incubated with the immobilized target molecules under agitation and the tube was thereafter washed in selection buffer.

Elution and Infection:

Phages from either solid or liquid phase selection were eluted with elution buffer (0.05 M glycine-HCl at pH 2.2, or 0.05 M NaAc buffer at pH 3.5, 3.8 or 4.5 as outlined in Table 1), followed by immediate neutralization with neutralization buffer (1 M Tris-HCl, pH 8.0). The eluted phages (95% of the volume) were used to infect log phase *E. coli* RR1ΔM15 cells (Rüther, Nucleic Acids Res 10:5765-5772, 1982) after each round of selection (approximately 500 times excess of cells compared to eluted phages). After 25 min incubation at 37° C., the cells were centrifuged. The pellet was dissolved in a small volume of TSB-YE (30 g/l tryptic soy broth, 5 g/l yeast extract) and spread on a TYE plate (15 g/l agar, 10 g/l tryptone water (Merck), 5 g/l yeast extract, 3 g/l NaCl, 2% glucose and 0.1 g/l ampicillin) and thereafter incubated over night at 37° C.

Preparation of Phage Stocks:

Phage Infected Cells Grown Over Night on TYE plates were re-suspended in TSB medium (30 g/l tryptic soy broth). An amount of suspended cells corresponding to approximately 100 infected cells of each eluted phage was inoculated in TSB-YE medium supplemented with 2% glucose and 100 mg/ml ampicillin. These cells were grown to log phase at 37° C. and a volume of them resembling the same amount of cells prior to growth were infected with 20 times excess of M13K07 helper phage (New England Biolabs, cat. no. NO315S). Cells and helper phage were incubated for 30 min at 37° C., and then pelleted by centrifugation, re-suspended in TSB-YE medium supplemented with 100 mM IPTG (isopropyl-6-D-1-thiogalacto-pyranoside), 25 µg/ml kanamycin and 100 µg/ml ampicillin and grown over night at 30° C. An aliquot of the re-suspended cells was stored at −20° C. as a glycerol stock.

The induced culture was centrifuged and phages in the supernatant were precipitated twice with a PEG/NaCl buffer (20% polyethyleneglycol, 2.5 M NaCl). The phages were re-suspended in selection buffer.

Phage stock and eluted phage were titrated after each round of selection.

ELISA Analysis of Binding

Proteins from clones obtained after four or five rounds of selection were produced in 96-well plates and screened for target binding activity using an ELISA setup.

Proteins were produced by inoculating single colonies in 1 ml TSB-YE medium supplemented with 100 µg/ml ampicillin and 1 mM IPTG in deep-well plates (Nunc, cat. no. 278752) and grown for 18-24 h at 37° C. A small amount of each culture was transferred to 96-well plates (Costar, cat. no. 9018) and stored at −20° C. as glycerol stocks. Remaining cells were pelleted by centrifugation, re-suspended in 400 µl PBS-T0.05 (PBS+0.05 Tween20) and frozen at −80° C. to release the periplasmic fraction of the cells. Frozen samples were thawed in a water bath and cells were pelleted by centrifugation. Supernatants containing soluble candidate IgG Fc-binding molecules fused to the albumin binding domain ABD from *Streptococcus* strain G148 were assayed for binding in an ELISA as follows.

Microtiter wells were coated with 100 µl of HSA at 6 µg/ml (Sigma, cat. no. J-1010) in coating buffer (0.1 M sodium carbonate, pH 9.5). The wells were blocked with 200 µl PBS-T0.05 complemented with 2% 0 dried milk for 1 h at room temperature. After removal of blocking, 100 ml of candidate IgG Fc-binding molecule solution was added in each well and the plates were incubated for 1.5 h at room temperature. Biotinylated IgG1κ (at a concentration of 0.05 and 0.5 µg/ml for clones derived from round 4 and 0.01 µg/ml for clones from round 5) or IgG Fc (at a concentration of 0.5 µg/ml; Jackson Immunoresearch, cat. no. 009-008, lot 66321) in 100 µl PBS-T0.05 was added to the wells and incubated for 1.5 h. Bound target was detected with SA-HRP (Dako, cat. no. P0397), diluted 1:5000 in PBS-T0.05, and incubated for 1 h at room temperature. Plates were washed four times with PBS-T0.05 before incubation with the biotinylated target, SA-HRP and developing solution. Developing solution was prepared by mixing of equal volumes of ImmunoPure TMB kit substrates TMB and $H_2O_2$ (Pierce, cat. no. 34021), and 100 µl were added to each well. After 30 min incubation in darkness, 100 µl stop solution (2 M $H_2SO_4$) was added. The plates were read at 450 nm in an ELISA spectrophotometer. All steps from blocking to reading were performed in a Tecan Genesis Freedom 200 robot.

Three controls were used:

Well F12: Positive control treated as above, but for plates with clones from selection round 4, a mixture of Z00000 (SEQ ID NO:10) and Z01730 (SEQ ID NO:11) as periplasmic fractions was used. For plates with clones from selection round 5, periplasmic fraction of Z00000 was used.

Well G12: Positive control. As described for well F12 but with biotinylated IgG1κ at a concentration of 1 µg/ml after round 4 and 0.5 µg/ml after round 5.

Well H12: Blank. PBS-T0.05 used instead of periplasmic fractions.

Sequencing of Potential Binders

Based on the ELISA results, clones were chosen for sequencing. For clones taken from selection round 4, clones with absorbance values similar to the positive control (well F12) were given priority. For clones taken from selection round 5, clones with the highest absorbance values were given priority. A high diversity among picked clones was desirable, and therefore many clones with different absorbance values were chosen from both screens.

PCR fragments were amplified from the chosen colonies using the oligonucleotides AFFI-21 (5'-tgcttccggctcgtatgttgtgtg-3') (SEQ ID NO:21) and AFFI-22 (5'-cggaaccagagccaccaccgg-3') (SEQ ID NO:22). Sequencing of amplified fragments was performed using BigDye Terminator v3.1 Cycle Sequencing Kit (Applied Biosystems, cat. no. 4336919) and the biotinylated oligonucleotide AFFI-72 (5'-biotin-cggaaccagagccaccaccgg-3') (SEQ ID NO:23) according to the manufacturer's recommendations. The sequencing reactions were purified by binding to magnetic streptavidin-coated beads (Magnetic Biosolutions, cat. no. 11103) using a Magnatrix 8000 (Magnetic Biosolutions), and analyzed on ABI PRISM 3100 Genetic Analyzer (Applied Biosystems). The sequencing results were imported and analyzed with Nautilus software (Thermo Electronics Corporation).

Results
Selection

Four different selection setups were applied and five selection rounds were made for each selection setup. Increasing numbers of washes and elution at different pH values were used in the selection setups.

ELISA

Clones obtained after four and five rounds of selection were produced in 96-well plates and screened for target binding activity using an ELISA setup. The putative IgG Fc-binding molecules were in periplasmic fractions obtained by freeze thawing.

In the ELISA screening of clones derived from the fourth selection rounds, IgG1κ and IgG Fc were used as targets at concentrations of 0.05 µg/ml and 0.5 µg/ml for IgG1κ and 0.5 µg/ml for IgG Fc. The ELISA results for round 4 clones indicated that absorbance values corresponded well between IgG1 and IgG Fc and were very high even at the low concentration of 0.05 µg/ml IgG1.

In the ELISA screening of clones derived from the fifth selection rounds, IgG1κ was used as target at a concentration of 0.01 µg/ml. The number of background binders was much higher among clones derived from round 5 as compared to clones from round 4. The responses were lowest among clones from the IgG_21 selection eluted with pH 4.5.

Sequencing

Clones from round 4 and 5 were sequenced, and the results compared with previously known protein Z variants. For the purposes of the present invention, one clone derived from round 4 (designated Z02674, SEQ ID NO:7; see FIG. 1) and two clones derived from round 5 (designated Z02726 and Z02742, SEQ ID NO:8 and SEQ ID NO:9, respectively; see FIG. 1) were chosen for further characterization.

In summary, the selections from the library ZLib2007-IgG were successful and suitable candidates were chosen for further characterization.

EXAMPLE 2

Further Characterization of IgG Fc-Binding Polypeptides

In this Example, a group of IgG Fc-binding polypeptides from the selection described in Example 1 were subcloned and expressed in monomeric form, and their binding characteristics studied.

Materials and Methods
Cultivation and Purification

IgG Fc-binding polypeptides Z02674, Z02726 and Z02742, as well as a modified version of Z02674 denoted Z02829, were sub-cloned as monomers into an expression vector in which expression is regulated by a T7 promoter. The IgG Fc-binding polypeptides were expressed with the additional N-terminal amino acid sequence GSSLQ and the additional C-terminal amino acid sequence VD. Thus, the expressed Z02674, Z02726 and Z02742 molecules have the sequence GSSLQ-[SEQ ID NO:#]-VD, wherein # corresponds to 7, 8 or 9 (see FIG. 1).

E. coli BL21(DE3) cells (Novagen) were transformed with the plasmids and cultivated at 37° C. in 1 l of TSB+YE medium (tryptic soy broth with yeast extract) supplemented with 50 µg/ml kanamycin. At $OD_{600}$=1, IPTG was added to induce protein expression at a final concentration of 1 mM and the cultivation was incubated at 37° C. for another 5 hours. The cells were harvested by centrifugation, re-suspended in 200 ml of binding buffer (50 mM sodium phosphate, 150 mM NaCl, pH 7.0) and sonicated to release the expressed protein. Cell debris was removed by centrifugation and the supernatant was applied on 40 ml IgG-sepharose in an XK26 column (GE Healthcare). Contaminants were washed away with binding buffer followed by elution of IgG Fc-binding molecules with elution buffer (0.1 M HAc). The purified IgG Fc-binding molecules were transferred to 10 mM $NH_4HCO_3$ by gel filtration and thereafter lyophilized. Concentration was determined using absorption at 280 nm and the extinction coefficient of the respective protein. The purity of the final product was analyzed on SDS PAGE stained with Coomassie Blue. The identity of the purified IgG Fc-binding molecules was confirmed using HPLC-MS.

Solubility Analysis

Lyophilized protein was dissolved in PBS. Protein solution was transferred to a plastic cuvette and examined for undissolved protein by visual inspection.

Circular Dichroism Analysis

CD analysis was performed with 0.5 mg/ml protein in PBS. A spectrum measurement at 195-250 nm was performed at 20° C. The melting point (Tm) of the purified proteins was determined by a variable temperature measurement (VTM) where 220 nm was monitored during heating of the sample to 90° C. After re-equilibrating the sample to 20° C., a new spectrum was taken. An overlay of spectrums before and after VTM showed if the structure was regained after heating to 90° C.

Binding Analysis

Binding of the purified molecules to human IgG was analyzed using surface plasmon resonance on a Biacore 2000 instrument (GE Healthcare). Etanercept (trade name Enbrel®, a fusion protein containing the Fc region of human IgG; Apoteket article no. 566661) and two human monoclonal IgG antibodies, palivizumab (trade name Synagis®, does not comprise a VH3 domain; Apoteket article no. 549170) and trastuzumab (trade name Herceptin®, comprises a VH3 domain: Apoteket article no. 573477) were used as target proteins. Target proteins were immobilized in different flow cells by amine coupling onto the carboxylated dextran layer on surfaces of CM-5 chips according to the manufacturer's recommendations. To analyze their binding to the immobilized target proteins, the purified IgG Fc-binding molecules were diluted in HBS-EP (0.01 M HEPES, 0.15 M NaCl, 3 mM EDTA, 0.005% surfactant P20, pH 7.2) and injected at 25 nM and 100 nM at a constant flow-rate of 25 µl/min for 4 minutes. The surfaces were regenerated with an injection of 0.3 M HAc, pH 3.2. An estimate of the dissociation equilibrium constant ($K_D$) was made using BIAevaluation 4.1 (GE Healthcare), assuming a one-to-one Langmuir binding model and taking mass transfer effects into account.

Size Exclusion Chromatography

Size exclusion chromatography (SEC) was performed to check for aggregates. The purified IgG Fc-binding molecules were diluted to 0.5 mg/ml in PBS and 50 µl was injected at the flow rate 0.5 ml/minute on a Superdex 75 10/300 GL column (GE Healthcare) equilibrated with PBS.

Results

Cultivation and Purification

Monomeric IgG Fc-binding molecules were expressed from plasmid vectors in E. coli. The total amount of IgG sepharose-purified protein from 1 liter-cultivations was determined spectrophotometrically at $A_{280}$ nm and is given in Table 2.

TABLE 2

Characteristics and amounts of purified proteins

| Protein | Molecular weight (Da) | 1 $A_{280}$ = (mg/ml) | Isoelectric point | Total amount (mg) |
|---------|----------------------|------------------------|-------------------|-------------------|
| Z02674  | 7321.1               | 1.05                   | 6.5               | 30                |
| Z02726  | 7321.2               | 1.05                   | 7.7               | nd                |
| Z02742  | 7341.2               | 1.05                   | 10.3              | 60                |

Lyophilized proteins were dissolved in PBS and 20 μg was analyzed with SDS-PAGE. All protein preparations contained IgG Fc-binding molecules together with some contaminating proteins. The size of the IgG Fc-binding molecules was confirmed with HPLC-MS.

Solubility Analysis

PBS was added to the lyophilized IgG Fc-binding molecules. Expected concentration based on the amount of protein in each vial is shown in Table 3.

TABLE 3

Expected concentration of dissolved molecules.

| Protein | Concentration (mg/ml) |
|---------|-----------------------|
| Z02674  | 18                    |
| Z02726  | 30                    |
| Z02742  | 30                    |

All three protein preparations contained precipitated contaminating material. For Z02674, undissolved material was removed by centrifugation and the supernatant was kept at +4° C. over night. A new visual inspection was performed, and no new precipitation could be seen. The concentration was measured with $A_{280}$ after centrifugation and found to be 17.4 mg/ml. For Z02726 and Z02742, the pH of the solutions was raised to approximately 10 with 50% NaOH, which resulted in a clear solution for both proteins.

Circular Dichroism Analysis

CD analysis was performed with the proteins Z02726, Z02742 and Z02829. Z02829 is a derivative of Z02674 containing two substitutions at the beginning of the protein (A8N and W11N with respect to the sequence of the entire expressed molecule, i.e. A3N and W6N with respect to SEQ ID NO:7). Thus, the IgG Fc-binding motif of Z02829 is the same as that of Z02674.

The determined melting points of the IgG Fc-binding molecules are given in Table 4.

TABLE 4

Determined melting points.

| Protein | $T_m$ (° C.) |
|---------|--------------|
| Z02829  | 62           |
| Z02726  | 62           |
| Z02742  | 63           |

Figure 2B:
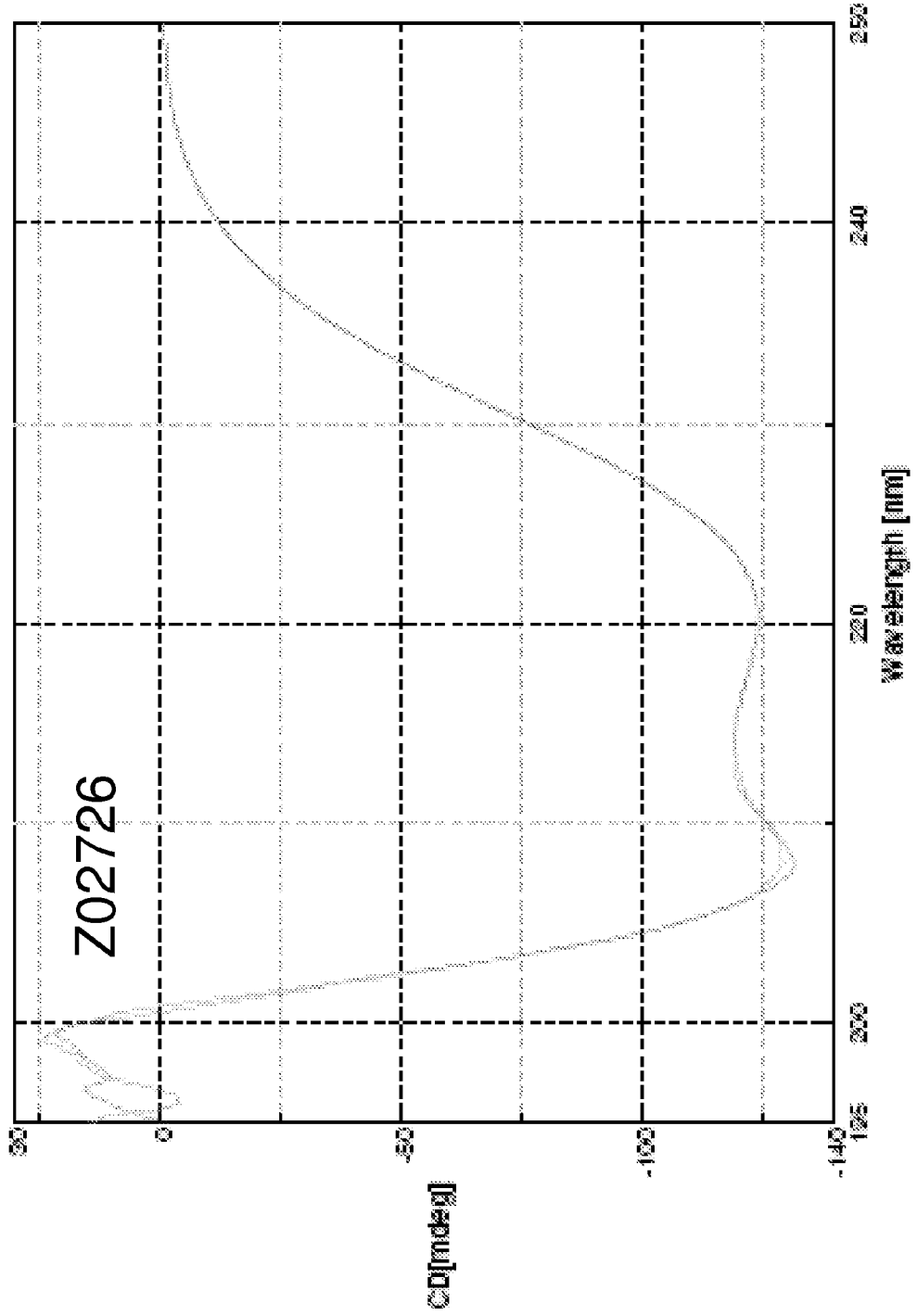
Figure 2C:
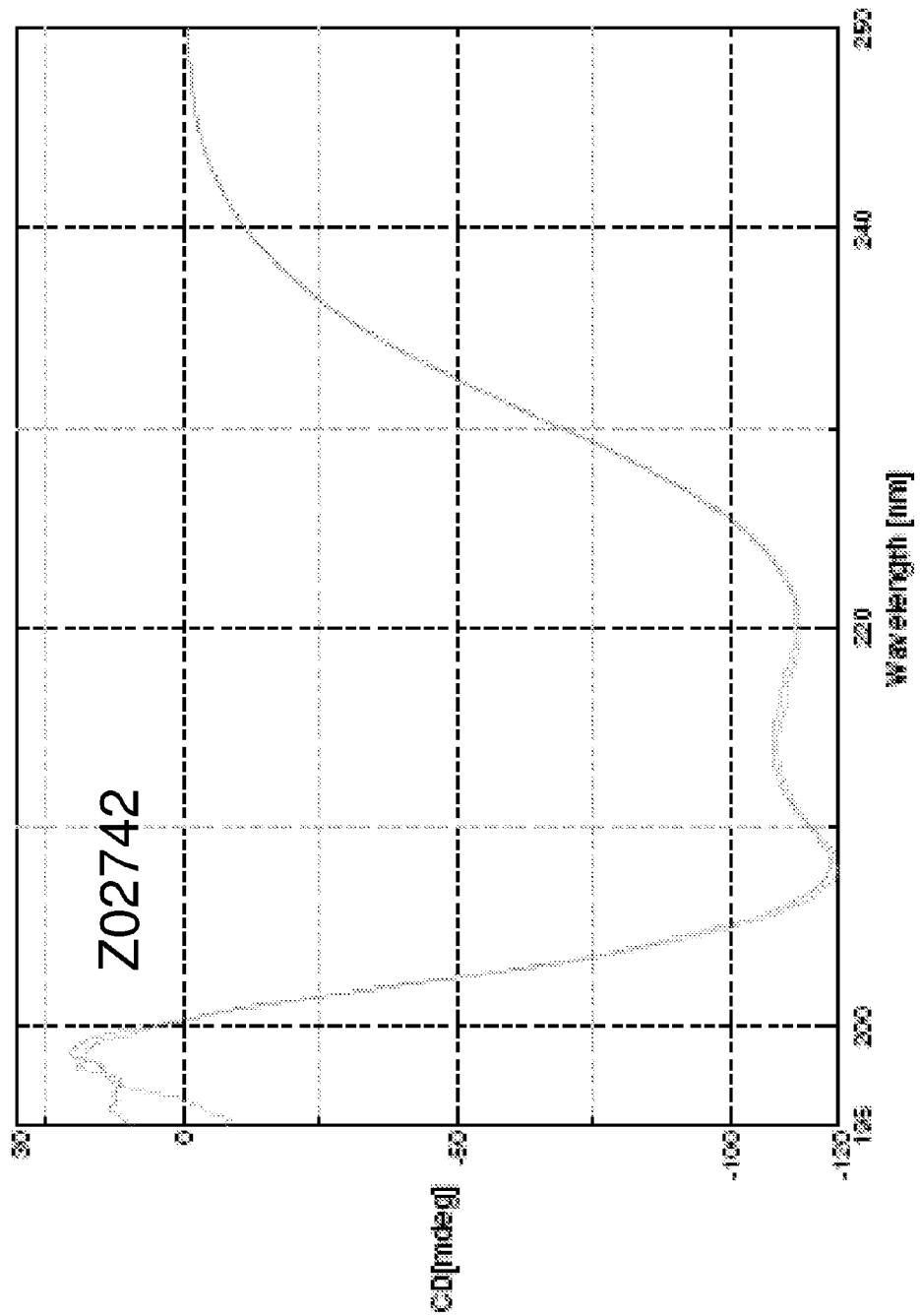
Figure 3A:
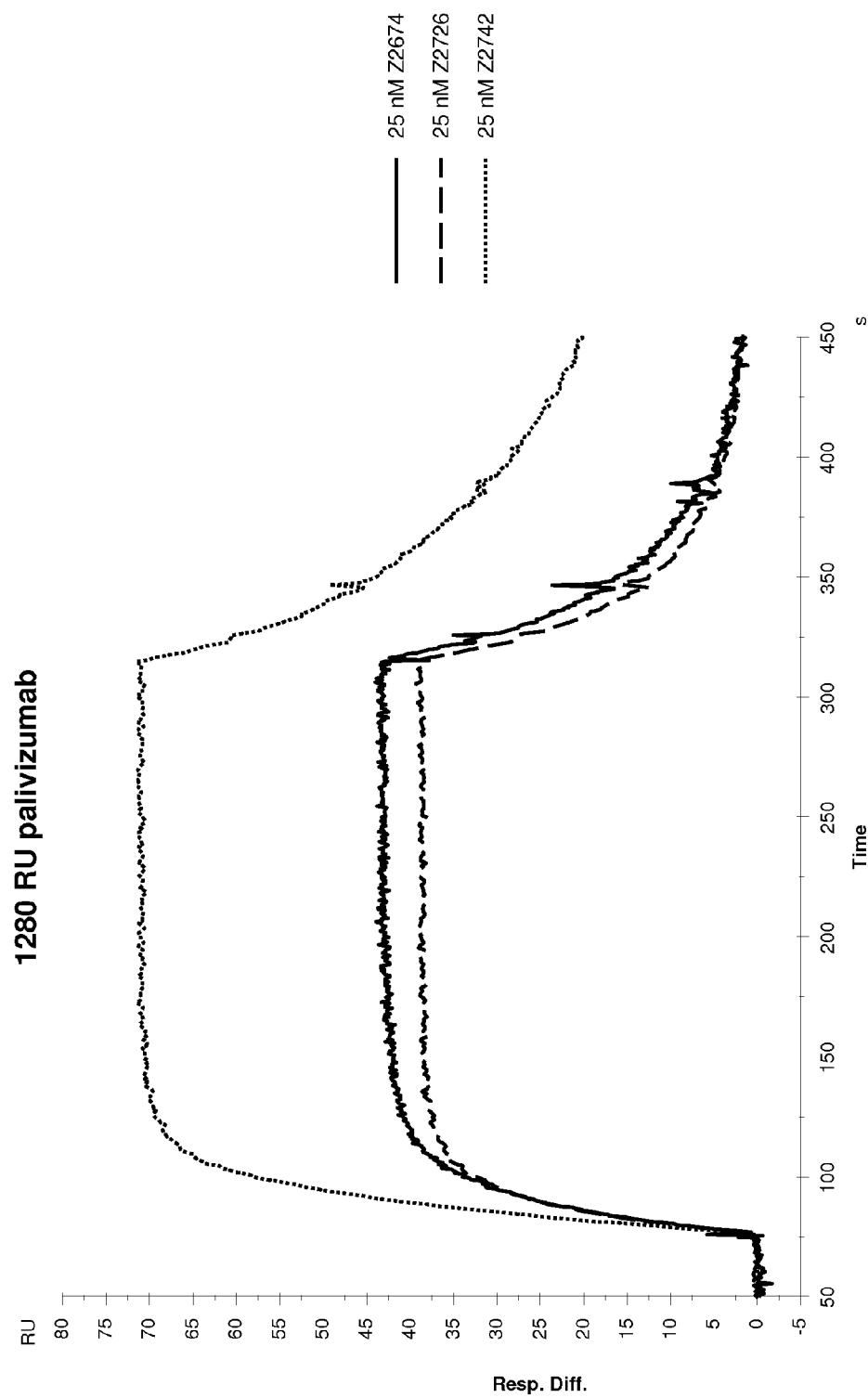
FIGS. 3A, 3B, and 3C show sensorgrams obtained from Biacore analysis of IgG Fc-binding molecules according to the invention. Sensorgrams obtained after injection of 25 nM of Z02674 (solid line), Z02726 (dashed line) or Z02742 (dotted line) over CM5 sensor-chip surfaces containing immobilized palivizumab (FIG. 3A; 1280 response units, RU); trastuzumab (FIG. 3B; 1200 RU) and etanercept (FIG. 3C; 1500 RU). Signal from a blank sensor-chip surface was subtracted.
Figure 3B:
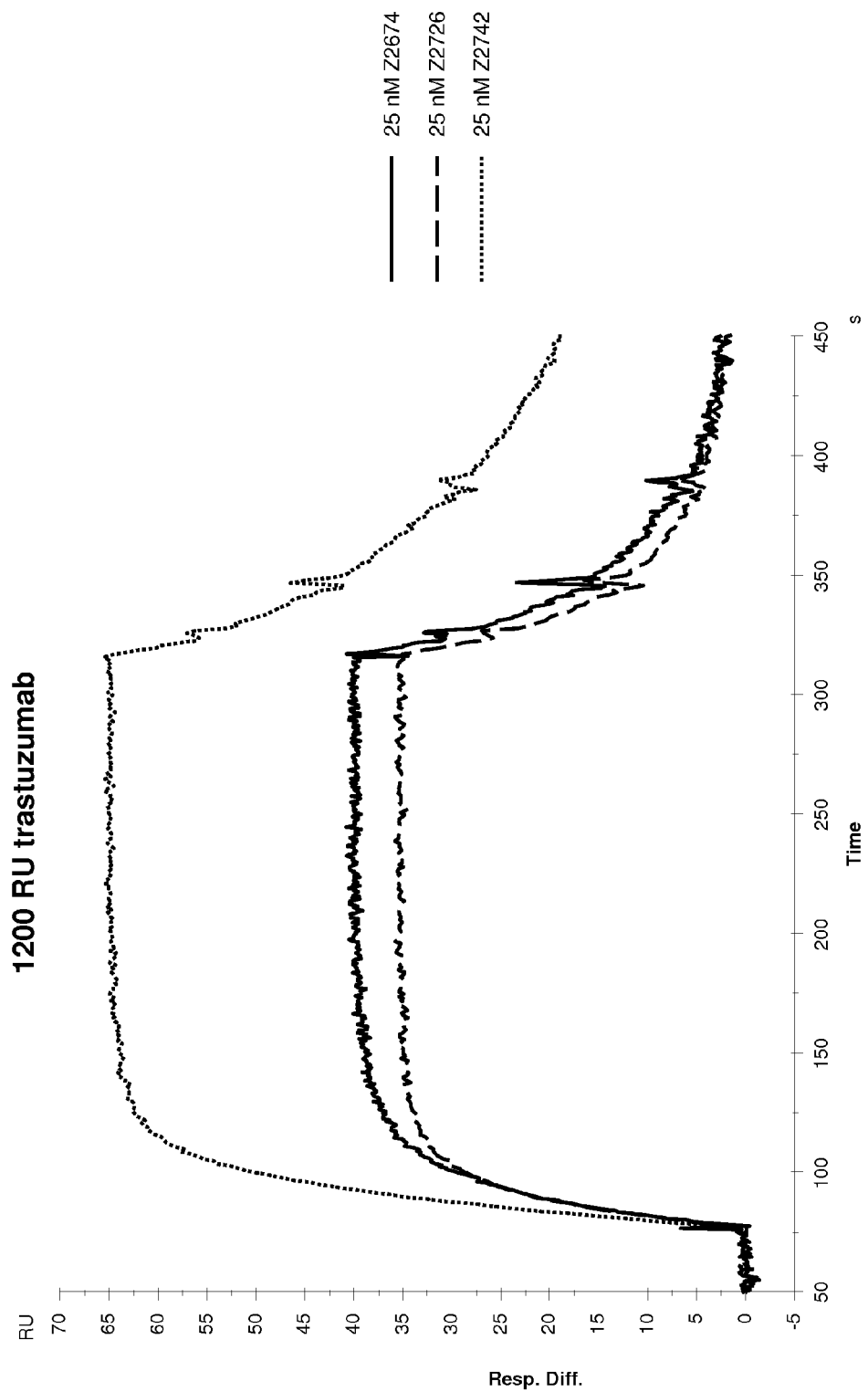
Figure 3C:
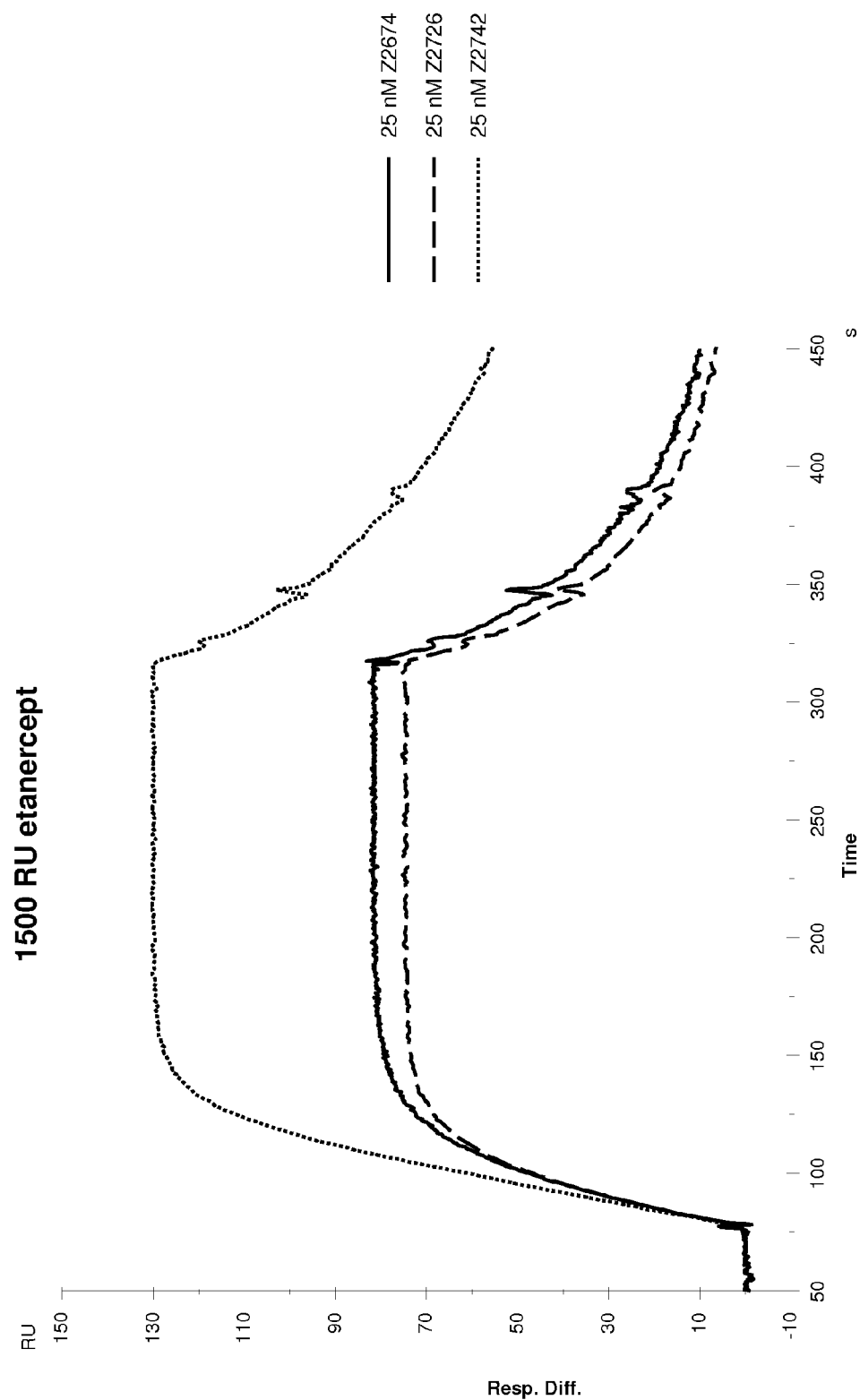
Figure 4A:
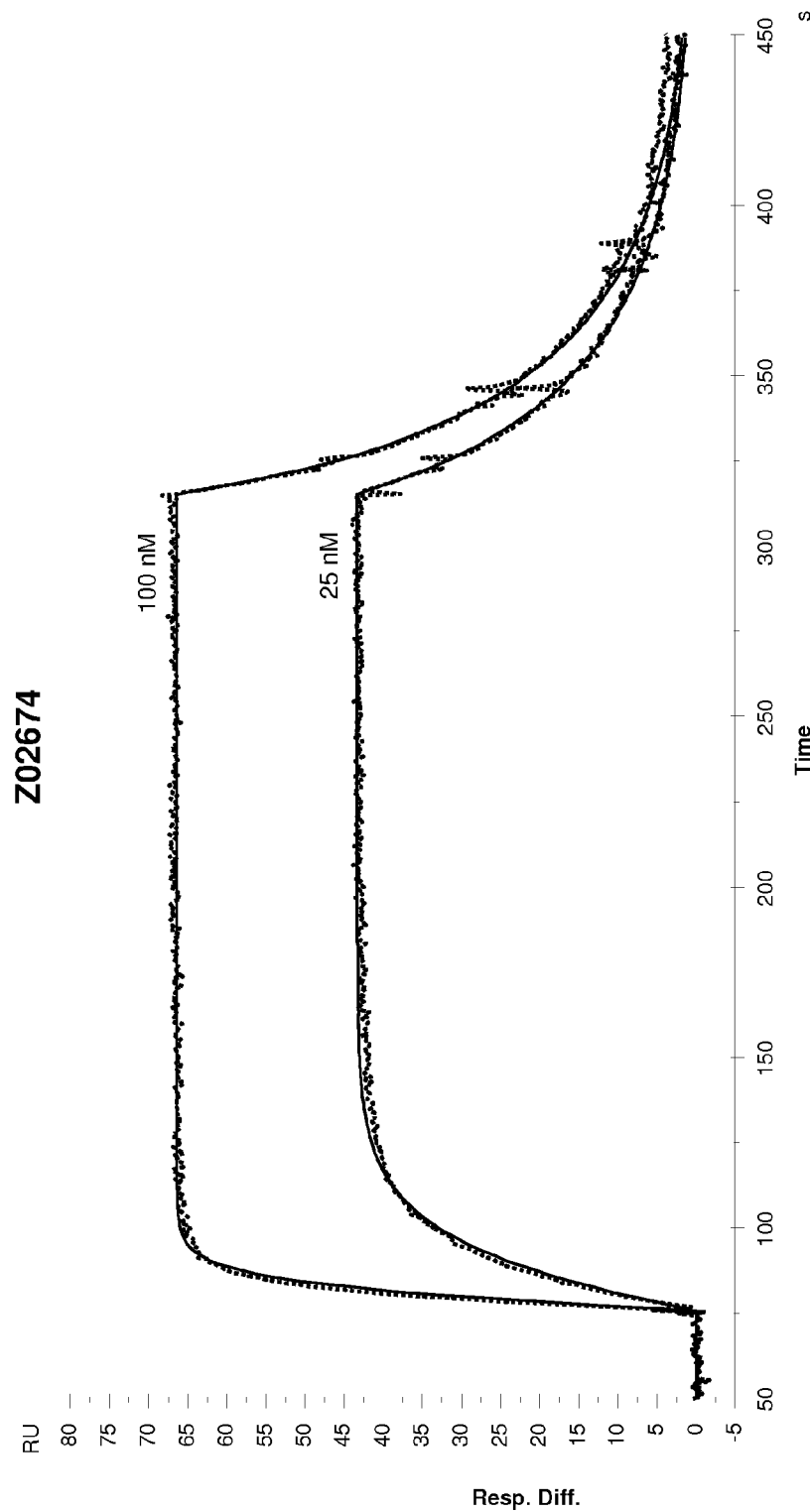
FIGS. 4A, 4B, and 4C show sensorgrams obtained from kinetic Biacore analysis of IgG Fc-binding molecules according to the invention. The overlay plots show sensorgrams obtained after injections over immobilized palivizumab of 25 nM or 100 nM of Z02674 (FIG. 4A); Z02726 (FIG. 4B) and Z02742 (FIG. 4C) (dotted lines). The response curves were fitted to a 1:1 binding model (solid lines).
Figure 4B:
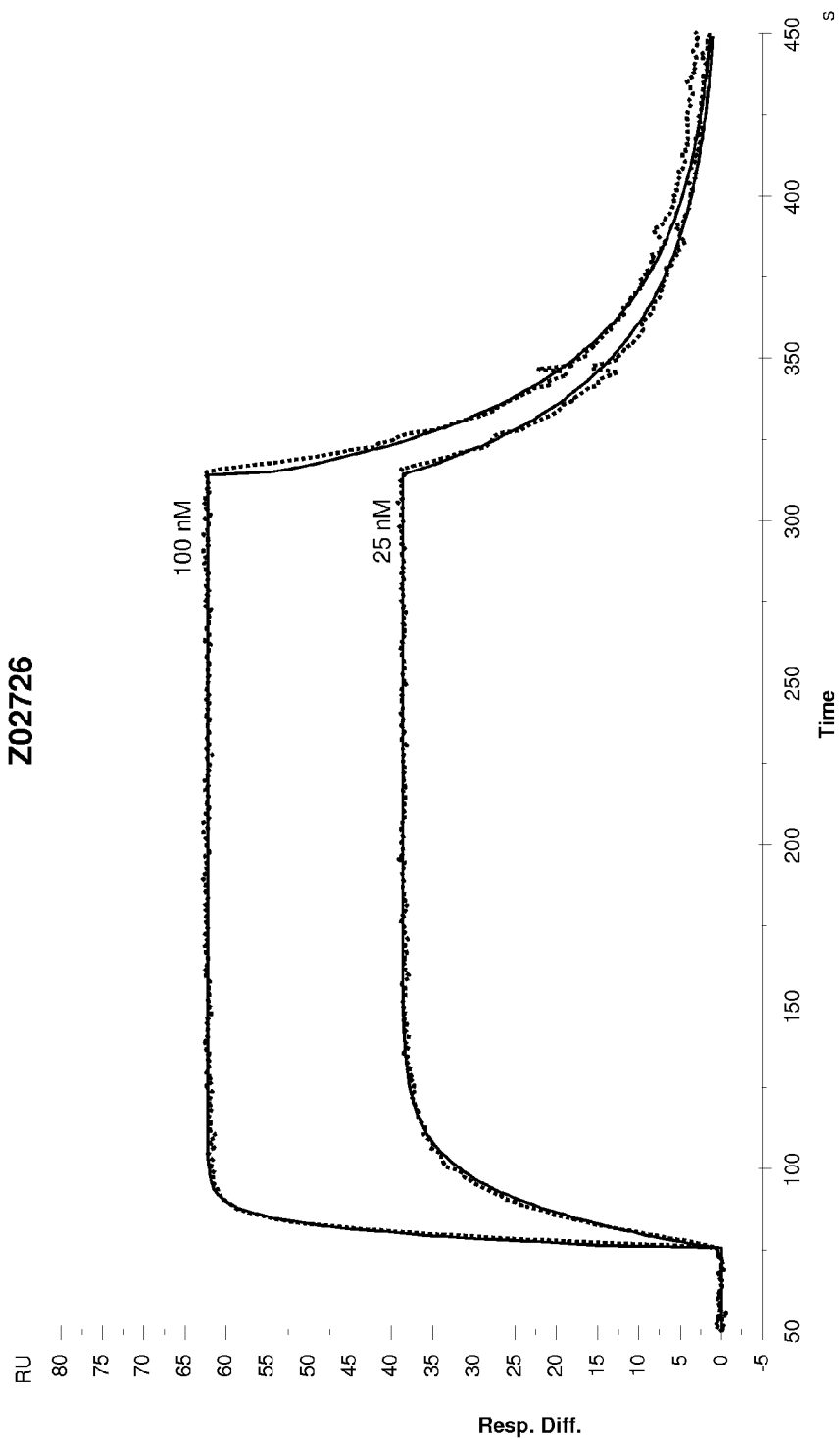
Figure 4C:
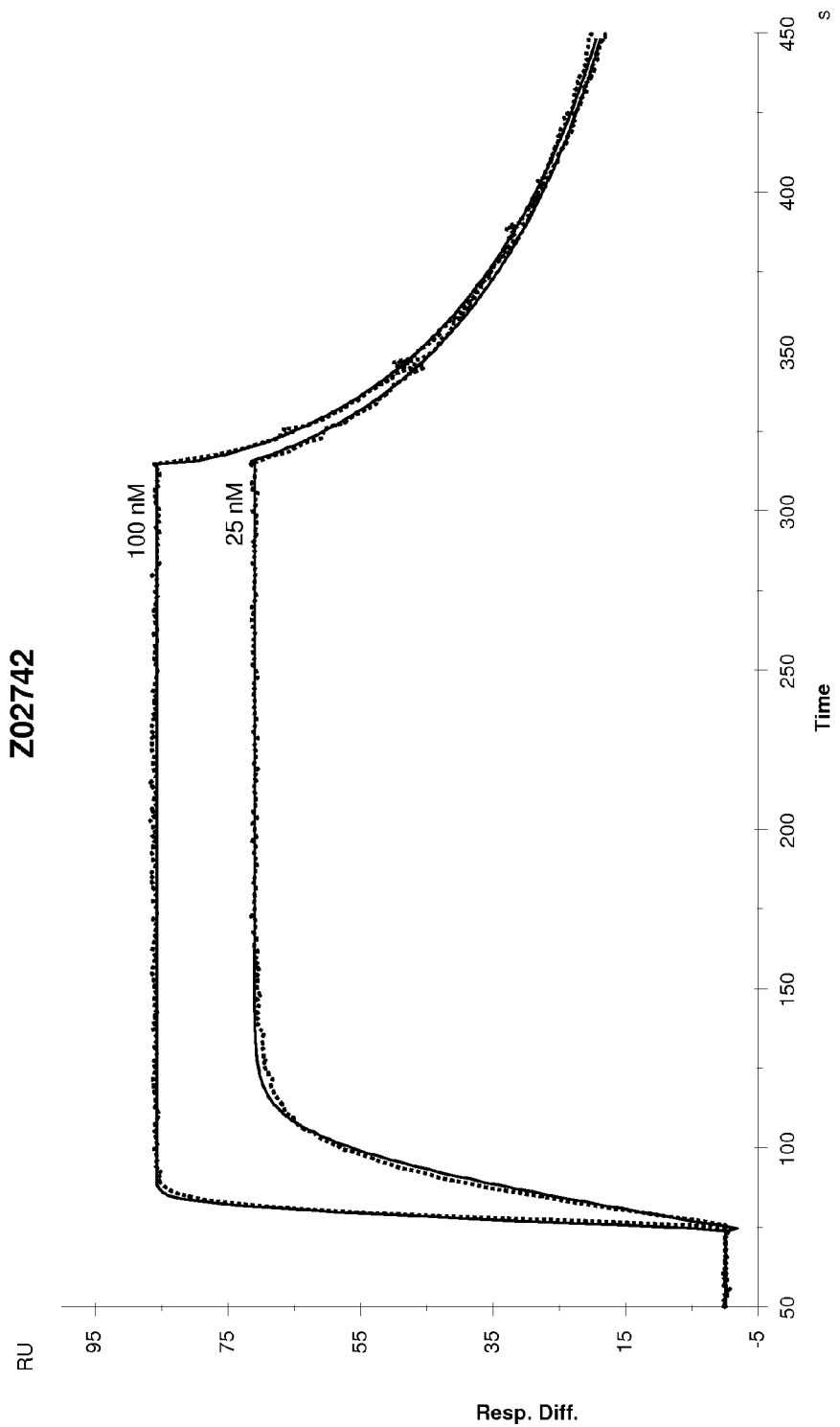

Overlay of spectra taken at 195-250 nm before and after VTM are shown in FIG. 2A-2C. As is evident from these overlay diagrams, all three IgG Fc-binding polypeptides completely regained their structure after heating at 90° C.

Binding Analysis

Binding of the purified polypeptides to human IgG Fc was analyzed using surface plasmon resonance on a Biacore 2000 instrument. Palivizumab (without VH3 domain), trastuzumab (with VH3 domain) and etanercept (TNFα-Fc fusion) were immobilized on chip surfaces with amine-coupling. The Z protein Z00000 (SEQ ID NO:10) and the earlier obtained variant Z01730 (SEQ ID NO:11) were used as controls. Binding diagrams for IgG Fc-binding molecules injected at 25 nM over immobilized target proteins are shown in FIGS. 3A-3C and FIGS. 4A-4C.

As evidenced in these Figures, all tested polypeptides bind to IgG.

In order to calculate an estimated binding affinity, the diagrams obtained from binding to palivizumab were analyzed with the BIAevaluation software provided by the manufacturer. The results are presented in Table 5. As shown in this Table, the IgG Fc-binding polypeptides exhibit binding affinities for IgG which are comparable to the positive control Z00000, which is a well known IgG Fc-binding molecule.

TABLE 5

Binding constants for selected IgG Fc-binding molecules

| Protein | $k_a$ (1/Ms) | $k_d$ (1/s) | $K_D$ (nM) |
|---------|--------------|-------------|------------|
| Z02674  | $2.4 \times 10^6$ | $5.2 \times 10^{-2}$ | 22 |
| Z02726  | $2.6 \times 10^6$ | $4.5 \times 10^{-2}$ | 18 |
| Z02742  | $9.6 \times 10^6$ | $4.3 \times 10^{-2}$ | 5  |
| Z00000 (control) | $3.6 \times 10^5$ | $4.9 \times 10^{-3}$ | 14 |

Size Exclusion Chromatography

SEC analysis was performed by injecting 100 μg of purified protein on a Superdex 75 10/300 GL column equilibrated with PBS. All IgG Fc-binding molecules eluted in single peaks. The shape of peaks differed between the IgG Fc-binding molecules and they elute at different times. However, they all elute later than Z00000, which indicates that there are no aggregates.

EXAMPLE 3

Affinity Chromatography Study of Elution pH and Capacity of IgG Fc-Binding Polypeptides In this Example, individual IgG Fc-binding polypeptides from the selection described in Example 1 were coupled to chromatoghraphic media, and their elution conditions and binding capacities were studied in affinity chromatography experiments.

Materials and Methods

Immobilization of IgG Fc-Binding Polypeptides

The inventive IgG Fc-binding polypeptides Z02742, Z02674 and Z02726 and the reference molecule Z00000 were each immobilized on NHS-activated HiTrap™ columns (0.962 ml, GE Healthcare). The immobilization, ligand coupling via primary amines, was performed in accordance with the manufacturer's instructions. Each polypeptide was immobilized on four columns, of which two were used for the elution pH study and two were used for the capacity study.

Buffer Preparation

Citric acid and NaCl (Merck) were dissolved in water to final concentrations of 0.1 M and 0.9 percent by weight (% wt/wt) respectively. Two buffers were prepared from this solution by adjusting pH to 6.2 for one part of the solution (buffer A) and to 2.5 for the other part of the solution (buffer B). pH adjustments were made by addition of NaOH. The buffers were filtered prior to use.

Elution Study

Elution pH was studied for three different samples run on columns comprising IgG Fc-binding polypeptide ligands.

The samples were trastuzumab (trade name Herceptin®, Apoteket article no. 573477), etanercept (trade name Enbrel®, Apoteket article no. 566661) and palivizumab (trade name Synagis®, Apoteket article no. 549113). The samples were prepared according to the manufacturer's instructions and were thereafter diluted to 1 mg/ml solutions in buffer A.

The columns were attached to an ÄKTA™ explorer 10 S chromatography system (GE Healthcare) and equilibrated (4 column volumes (CV) buffer A, flow rate 1 ml/min). Sample solution was injected into a Superloop™ (50 ml, GE Healthcare) and 2 ml were loaded on each column at a flow rate of 0.4 ml/min. The columns were washed (3 CV buffer A, 1 ml/min) and the sample was eluted by an acidic pH gradient (25 CV, 0-100% buffer B, 1 ml/min). After the acidic pH gradient, the columns were washed (4 CV 100% buffer B, 1 ml/min) and re-equilibrated (4 CV buffer A, 1 ml/min).

Eluted samples were collected with a fraction collector (Frac-950, GE Healthcare) in order to allow pH measurements in the eluted fractions. Peaks were collected when the absorbance at 280 nm ($A_{280}$) exceeded 5% of $A_{280}$ for the 1 mg/ml sample solution. Peak collection stopped when the absorbance fell below the same 5% threshold.

Capacity Study

Dynamic binding capacity for a chromatographic medium is usually defined as the amount of sample applied to the medium when the absorbance at 280 nm reaches 10% of the sample absorbance at 280 nm. The capacity was determined by loading sample on columns comprising immobilized IgG Fc-binding polypeptides. To determine the capacity, the dead volume (i.e. tubing and column volume) was subtracted from the sample volume required for 10% breakthrough. The dead volume was measured by running sample through a column comprising no IgG Fc-binding polypeptide.

Human polyclonal IgG (trade name Gammanorm®, Apoteket article no. 096169, comprising a mix of VH3 subfamily and non-VH3 subfamily antibodies) was used for determining capacity. The IgG sample was prepared by diluting 165 mg/ml Gammanorm® to 0.75 mg/ml with 1×PBS.

The columns were attached to an ÄKTA™ explorer 10 S chromatography system (GE Healthcare) and equilibrated (4 CV buffer A, 1 ml/min). The sample was loaded on the columns with a flow rate of 0.241 ml/min (residence time 4 min) until $A_{280}$ reached 10% (in this case 128.2 mAU) of the sample absorbance. Bound protein was eluted (10 CV buffer B, 1 ml/min) and the columns were re-equilibrated (4 CV buffer A, 1 ml/min).

Results

Elution Study

Figure 5A:
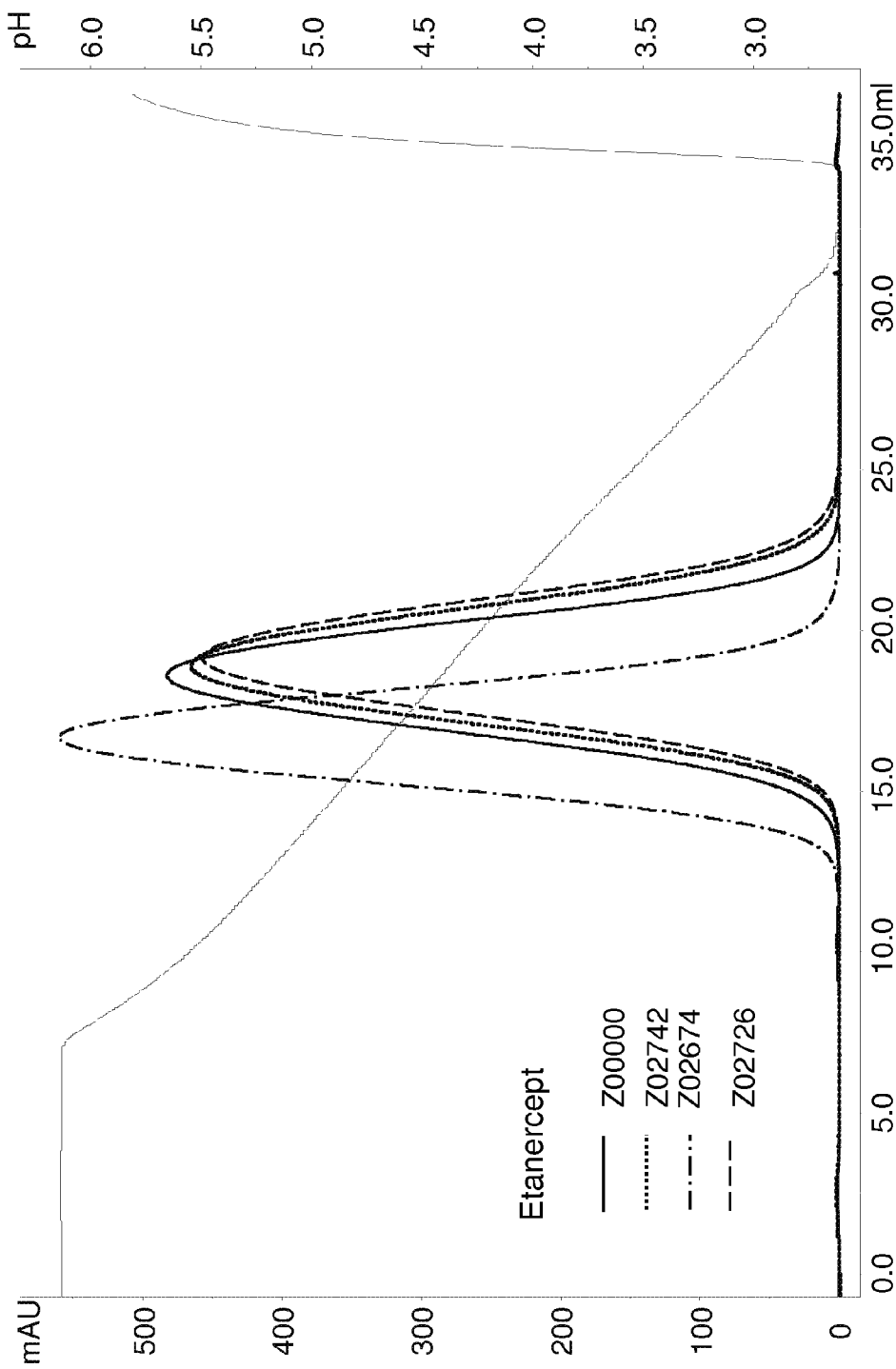
FIGS. 5A, 5B, and 5C show chromatograms for columns comprising immobilized IgG Fc-binding polypeptides according to the invention. The overlay chromatograms show elution profiles for etanercept (FIG. 5A), trastuzumab (FIG. 5B) and palivizumab (FIG. 5C) when eluted with an acidic pH gradient from columns comprising Z00000, Z02742, Z02674 or Z02726, as indicated.
Figure 5B:
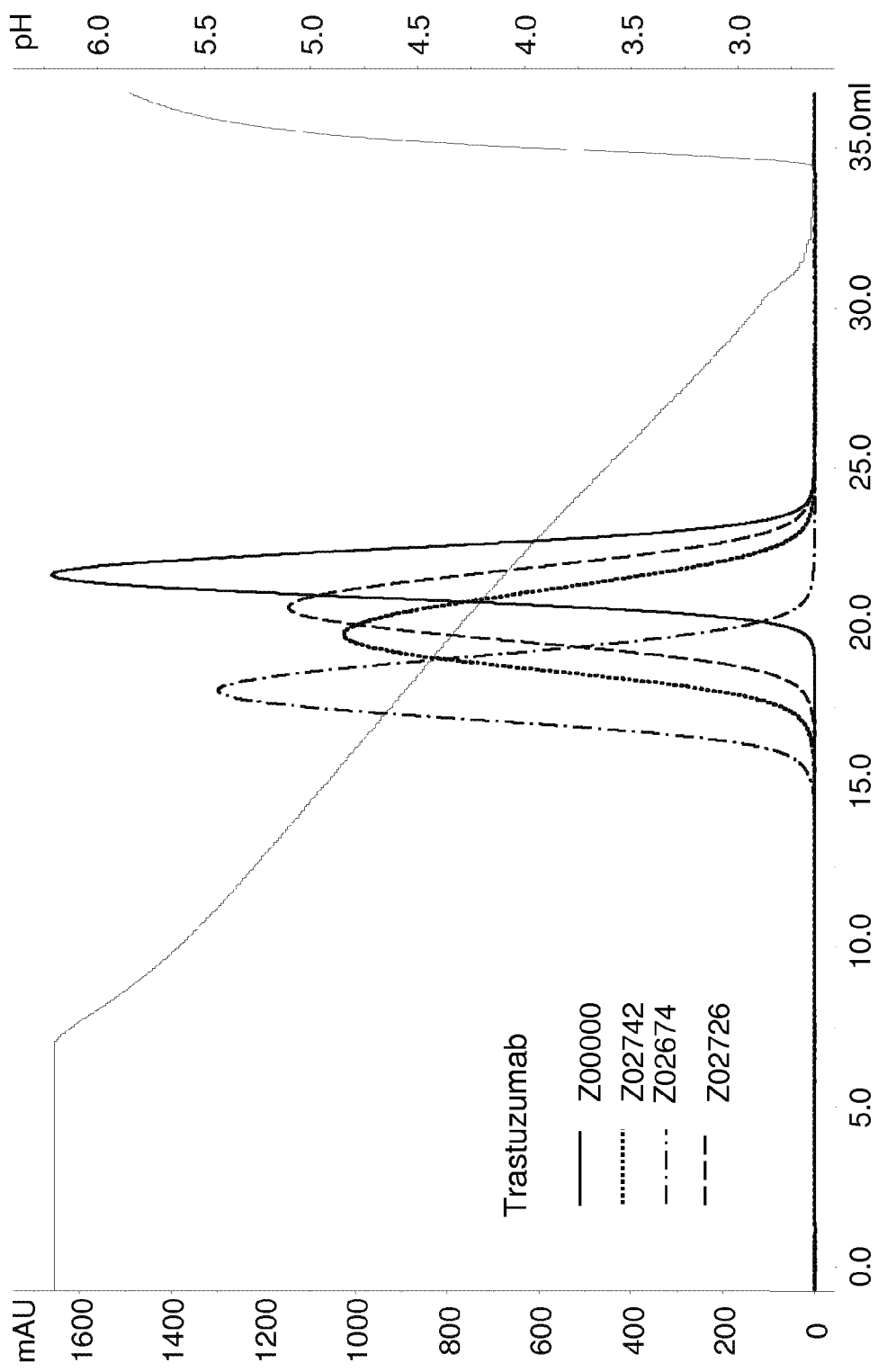
Figure 5C:
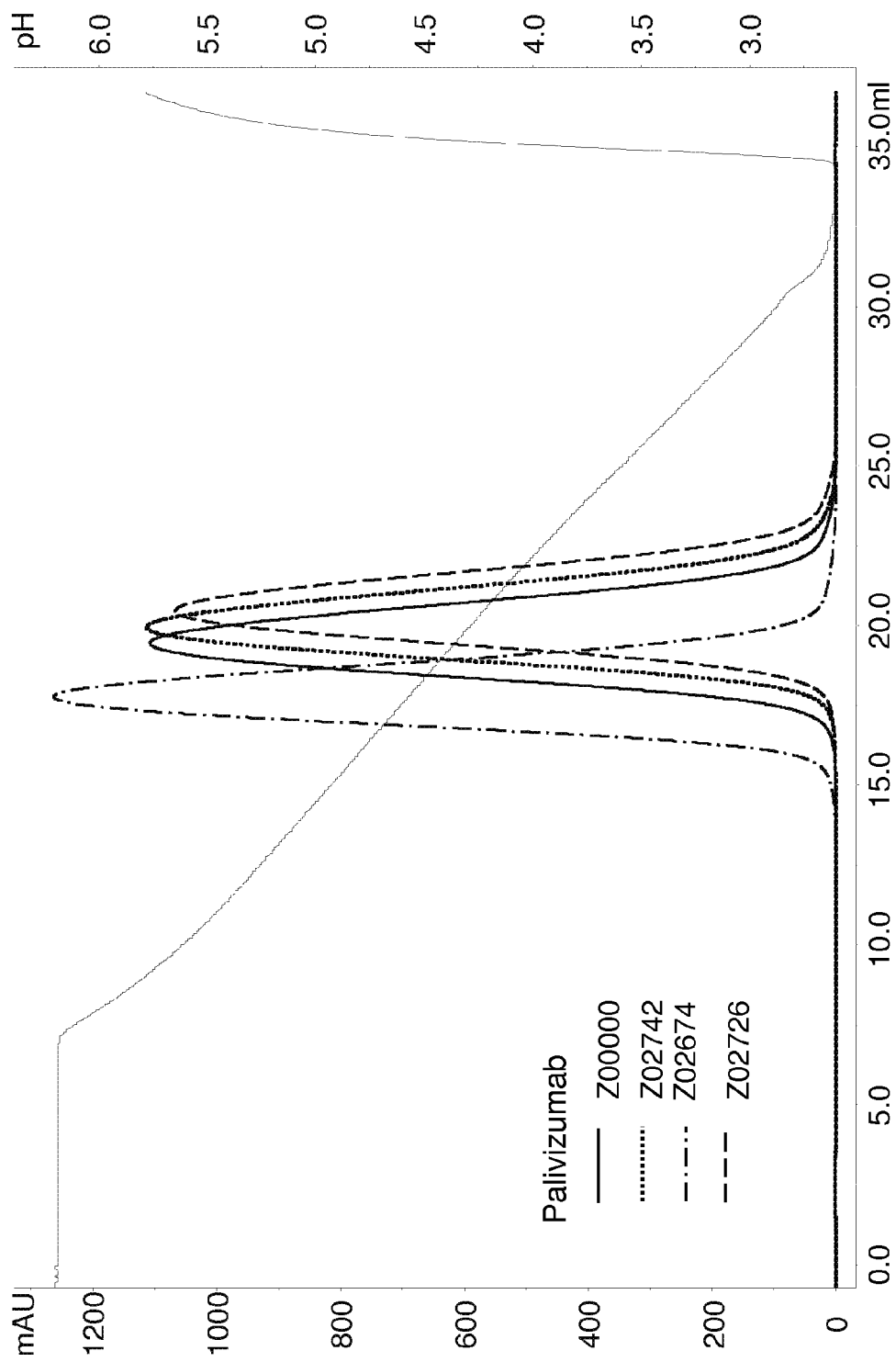

All samples were eluted at a higher pH (i.e. earlier in the gradient) from the columns comprising immobilized Z02674 than from the columns comprising the other polypeptide ligands. Trastuzumab was eluted from columns comprising Z00000 at a lower pH (i.e. later in the gradient) than from the other columns. Thus, pH in eluted fractions of trastuzumab were higher from the columns comprising the IgG Fc-binding polypeptides according to the invention than from the columns comprising the reference molecule Z00000. Overlays of chromatograms for different columns are shown in FIGS. 5A-C.

Thus, the tested IgG Fc-binding polypeptides according to the invention bind to IgG and exhibit elution profiles in affinity chromatography which are comparable to, or better than, those of the column-coupled reference molecule Z00000.

Capacity Study

Figure 6:
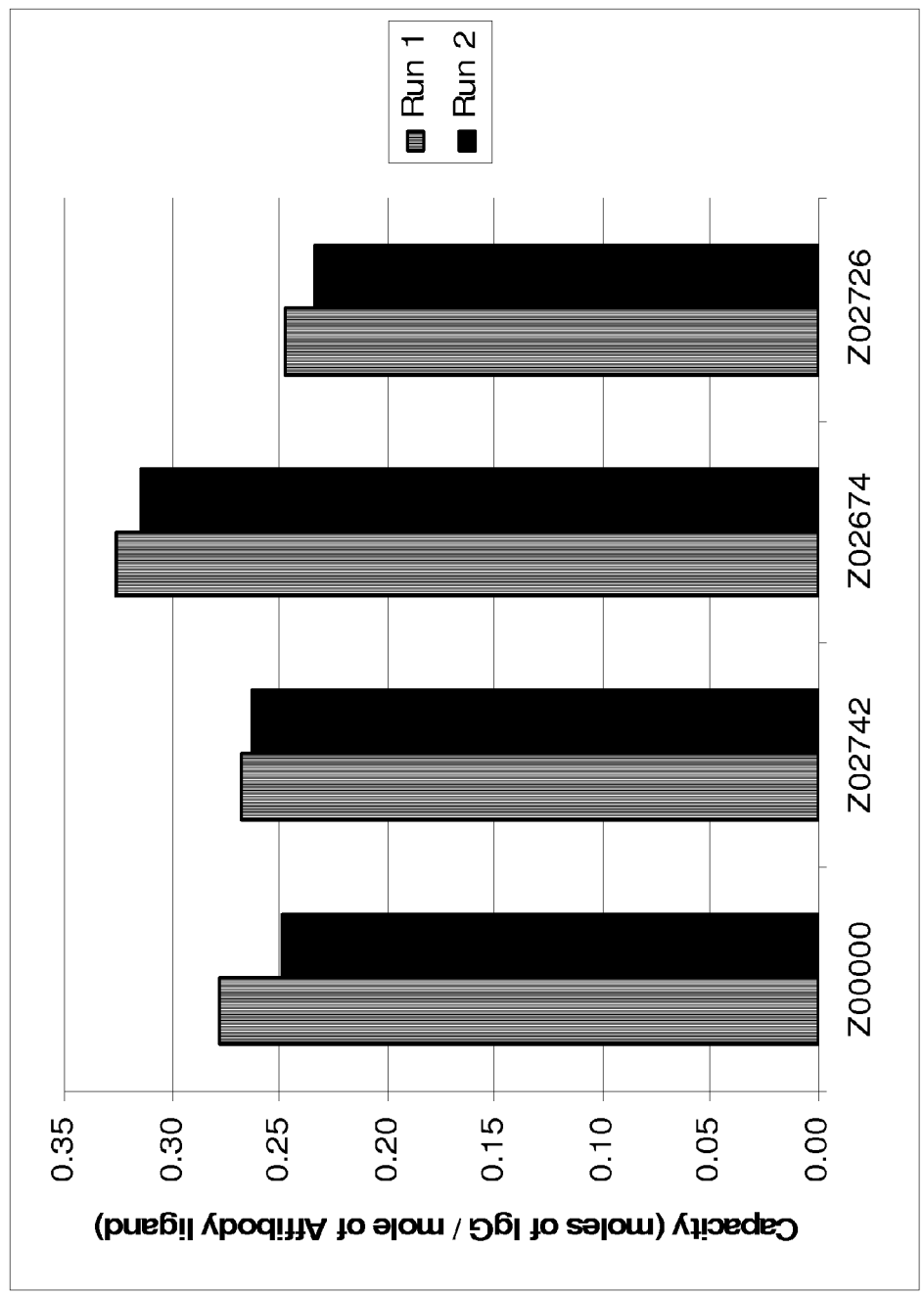
FIG. 6 shows a histogram of dynamic binding capacities (moles of IgG/moles of polypeptide) for columns comprising immobilized Z00000, Z02742, Z02674 or Z02726, as indicated.

Capacities of the column-coupled IgG Fc binding polypeptides according to the invention ranged from 0.23 to 0.33 moles of IgG/moles polypeptide ligand and were comparable with the capacities of column-coupled Z00000 (see FIG. 6). The dynamic binding capacity of columns comprising immobilized Z02674 was, however, approximately 20-30% higher than for the other columns.

The invention claimed is:

1. An Immunoglobulin G Fc (IgG Fc) binding polypeptide, comprising an immunoglobulin G Fc (IgG Fc) binding motif (BM) which motif consists of an amino acid sequence selected from:

$$\text{EQQX}_4\text{AFYEIL HLPNLTEX}_{18}\text{QX}_{20} \text{ X}_{21}\text{AFIX}_{25}\text{X}_{26}\text{LRX}_{29} \quad \text{(SEQ ID NO: 12)}$$

wherein, independently of each other,
$X_4$ is selected from H and N;
$X_{18}$ is selected from D and G;
$X_{20}$ is selected from R and K;
$X_{21}$ is selected from H and Q;
$X_{25}$ is selected from R, A and G;
$X_{26}$ is selected from A, S and T; and
$X_{29}$ is selected from G, K and A;

wherein said IgG Fc-binding polypeptide binds to IgG Fc such that the $K_D$ value of the interaction is at most $1 \times 10^{-6}$ M; and wherein said IgG Fc binding motif forms part of a three-helix bundle protein domain.

2. The IgG Fc-binding polypeptide according to claim 1, wherein $X_4$ is H.

3. The IgG Fc-binding polypeptide according to claim 1, wherein $X_{18}$ is G.

4. The IgG Fc-binding polypeptide according to claim 1, wherein $X_{20}$ is K.

5. The IgG Fc-binding polypeptide according to claim 1, wherein $X_{21}$ is H.

6. The IgG Fc-binding polypeptide according to claim 1, wherein $X_{25}$ is R.

7. The IgG Fc-binding polypeptide according to claim 1, wherein $X_{26}$ is A.

8. The IgG Fc-binding polypeptide according to claim 1, wherein $X_{29}$ is G.

9. The IgG Fc-binding polypeptide according to claim 1, wherein the amino acid sequence is selected from the group consisting of SEQ ID NO: 1, SEQ ID NO: 2, and SEQ ID NO: 3.

10. The IgG Fc-binding polypeptide according to claim 9, wherein the amino acid sequence is SEQ ID NO: 1.

11. The IgG Fc-binding polypeptide according to claim 1, in which said IgG Fc-binding motif forms part of two alpha helices and a loop connecting them, within said three-helix bundle protein domain.

12. The IgG Fc-binding polypeptide according to claim 11, in which said three-helix bundle protein domain is selected from domains of bacterial receptor proteins.

13. The IgG Fc-binding polypeptide according to claim 12, in which said three-helix bundle protein domain is selected from domains of protein A from *Staphylococcus aureus* or derivatives thereof.

14. The IgG Fc-binding polypeptide according to claim 12, which comprises an amino acid sequence selected from:

```
                                      (SEQ ID NO: 13)
a) ADNNFNK-[BM]-DPSQSANLLSEAKKLNESQAPK;

(SEQ ID NO: 14)
b) ADNKFNK-[BM]-DPSQSANLLAEAKKLNDAQAPK;

(SEQ ID NO: 15)
c) ADNKFNK-[BM]-DPSVSKEILAEAKKLNDAQAPK, (SEQ ID NO: 16)
d) ADAQQNNFNK-[BM]-DPSQSTNVLGEAKKLNESQAPK;

(SEQ ID NO: 17)
e) AQHDE-[BM]-DPSQSANVLGEAQKLNDSQAPK;
and (SEQ ID NO: 18)
f) VDNKFNK-[BM]-DPSQSANLLAEAKKLNDAQAPK;
``` wherein BM is an IgG Fc-binding motif, and wherein the motif consists of an amino acid sequence selected from:

```
                                      (SEQ ID NO: 12)
EQQX₄AFYEIL HLPNLTEX₁₈QX₂₀ X₂₁AFIX₂₅X₂₆LRX₂₉
``` wherein, independently of each other,
$X_4$ is selected from H and N;
$X_{18}$ is selected from D and G;
$X_{20}$ is selected from R and K;
$X_{21}$ is selected from H and Q;
$X_{25}$ is selected from R, A and G;
$X_{26}$ is selected from A, S and T; and
$X_{29}$ is selected from G, K and A;
wherein said IgG Fc-binding polypeptide binds to IgG Fc such that the $K_D$ value of the interaction is at most $1 \times 10^{-6}$ M; and
wherein said IgG Fc binding motif forms part of a three-helix bundle protein domain.

15. The IgG Fc-binding polypeptide according to claim 11, which comprises the amino acid sequence:

```
                                      (SEQ ID NO: 19)
FWK-[BM]-DPSQSARLLA Xₐ AKKLDDAQ
```

Wherein BM is an IgG Fc-binding motif, and wherein the motif consists of an amino acid sequence selected from:

```
                                      (SEQ ID NO: 12)
EQQX₄AFYEIL HLPNLTEX₁₈QX₂₀ X₂₁AFIX₂₅X₂₆LRX₂₉
``` wherein, independently of each other,
$X_4$ is selected from H and N;
$X_{18}$ is selected from D and G;
$X_{20}$ is selected from R and K;
$X_{21}$ is selected from H and Q;
$X_{25}$ is selected from R, A and G;
$X_{26}$ is selected from A, S and T; and
$X_{29}$ is selected from G, K and A;
wherein said IgG Fc-binding polypeptide binds to IgG Fc such that the $K_D$ value of the interaction is at most $1 \times 10^{-6}$ M;
wherein said IgG Fc binding motif forms part of a three-helix bundle protein domain; and
wherein $X_a$ is selected from R, G and Q.

16. The IgG Fc-binding polypeptide according to claim 15, wherein $X_a$ is R.

17. The IgG Fc-binding polypeptide according to claim 15, which comprises an amino acid sequence selected from the group consisting of SEQ ID NO: 4, SEQ ID NO: 5, and SEQ ID NO: 6.

18. The IgG Fc-binding polypeptide according to claim 17, which comprises the amino acid sequence SEQ ID NO: 4.

19. The IgG Fc-binding polypeptide according to claim 11, which comprises the amine acid sequence:

```
                                      (SEQ ID NO: 20)
VDAKFWK-[BM]-DPSQSARLLA Xₐ AKKLDDAQAPK
```

Wherein BM is an IgG Fc-binding motif, and wherein the motif consists of an amino acid sequence selected from:

```
                                      (SEQ ID NO: 12)
EQQX₄AFYEIL HLPNLTEX₁₈QX₂₀ X₂₁AFIX₂₅X₂₆LRX₂₉
``` wherein, independently of each other,
$X_4$ is selected from H and N;
$X_{18}$ is selected from D and G;
$X_{20}$ is selected from R and K;
$X_{21}$ is selected from H and Q;
$X_{25}$ is selected from R, A and G;
$X_{26}$ is selected from A, S and T; and
$X_{29}$ is selected from G, K and A;
wherein said IgG Fc-binding polypeptide binds to IgG Fc such that the $K_D$ value of the interaction is at most $1 \times 10^{-6}$ M;
wherein said IgG Fc binding motif forms part of a three-helix bundle protein domain; and
wherein $X_a$ is selected from R, G and Q.

20. The IgG Fc-binding polypeptide according to claim 19, wherein $X_a$ is R.

21. The IgG Fc-binding polypeptide according to claim 1, which binds to IgG Fc such that the $K_D$ value of the interaction is at most $1 \times 10^{-7}$ M.

22. The IgG Fc-binding polypeptide according to claim 21, which binds to IgG Fc such that the $K_D$ value of the interaction is at most $5 \times 10^{-8}$ M.

23. An IgG Fc-binding polypeptide, comprising an amino acid sequence selected from the group consisting of SEQ ID NOs: 7-9.

24. The IgG Fc-binding polypeptide according to claim 23, wherein the amino acid is SEQ ID NO: 7.

25. The IgG Fc-binding polypeptide according to claim 23, comprising additional amino acid residues C terminally and/or N terminally with respect to said IgG Fc-binding polypeptide.

26. The IgG Fc-binding polypeptide according to claim 25, in which each amino acid extension enhances binding of IgG Fc by the polypeptide.

27. The IgG Fc-binding polypeptide according to claim 25, in which each amino acid extension improves production, purification, stabilization in vivo or in vitro, coupling, or detection of the polypeptide.

28. The IgG Fc-binding polypeptide according to claim 1 or 23, which is capable of binding to the Fc portion of a human IgG molecule.

29. The IgG Fc-binding polypeptide according claim 28, which is capable of binding to classes 1, 2 and 4 of human IgG.

30. The IgG Fc-binding polypeptide according to claim 1 or 23, which is capable of binding to the interface between the CH2 and CH3 domains of IgG Fc.

31. The IgG Fc-binding polypeptide according to claim 1 or 23, which is capable of binding to an area on the Fc molecular surface made up by the Fc amino acid residues T250-S254, T256, L309-L312, L314, D315, E430 and L432-Y436 of the human Fc fragment amino acid sequence.

32. The IgG Fc-binding polypeptide according to claim 1 or 23 in multimeric form, comprising at least two IgG Fc-binding polypeptide monomer units, whose amino acid sequences may be the same or different.

33. The IgG Fc-binding polypeptide according to claim 32, in which the IgG Fc-binding polypeptide monomer units are covalently coupled together.

34. The IgG Fc-binding polypeptide according to claim 33, in which the IgG Fc-binding polypeptide monomer units are expressed as a fusion protein.

35. The IgG Fc-binding polypeptide according to claim 32, in which the IgG Fc-binding polypeptide monomer units are expressed as a fusion protein.

36. An Affinity chromatography medium, comprising an IgG Fc-binding polypeptide according to claim 1 or 23.

\* \* \* \* \*

SEQUENCE LISTING

```
<160> NUMBER OF SEQ ID NOS: 23

<210> SEQ ID NO 1
<211> LENGTH: 29
<212> TYPE: PRT
<213> ORGANISM: Artificial Sequence
<220> FEATURE:
<223> OTHER INFORMATION: IgG Fc-binding polypeptide

<400> SEQUENCE: 1

Glu Gln Gln Asn Ala Phe Tyr Glu Ile Leu His Leu Pro Asn Leu Thr
1               5                   10                  15

Glu Asp Gln Arg His Ala Phe Ile Gly Thr Leu Arg Ala
            20                  25

<210> SEQ ID NO 2
<211> LENGTH: 29
<212> TYPE: PRT
<213> ORGANISM: Artificial Sequence
<220> FEATURE:
<223> OTHER INFORMATION: IgG Fc-binding polypeptide

<400> SEQUENCE: 2

Glu Gln Gln His Ala Phe Tyr Glu Ile Leu His Leu Pro Asn Leu Thr
1               5                   10                  15

Glu Asp Gln Arg Gln Ala Phe Ile Ala Ser Leu Arg Lys
            20                  25
```

<210> SEQ ID NO 3
<211> LENGTH: 29
<212> TYPE: PRT
<213> ORGANISM: Artificial Sequence
<220> FEATURE:
<223> OTHER INFORMATION: IgG Fc-binding polypeptide

<400> SEQUENCE: 3

Glu Gln Gln His Ala Phe Tyr Glu Ile Leu His Leu Pro Asn Leu Thr
1               5                   10                  15

Glu Gly Gln Lys His Ala Phe Ile Arg Ala Leu Arg Gly
            20                  25

<210> SEQ ID NO 4
<211> LENGTH: 51
<212> TYPE: PRT
<213> ORGANISM: Artificial Sequence
<220> FEATURE:
<223> OTHER INFORMATION: IgG Fc-binding polypeptide

<400> SEQUENCE: 4

Phe Trp Lys Glu Gln Gln Asn Ala Phe Tyr Glu Ile Leu His Leu Pro
1               5                   10                  15

Asn Leu Thr Glu Asp Gln Arg His Ala Phe Ile Gly Thr Leu Arg Ala
            20                  25                  30

Asp Pro Ser Gln Ser Ala Arg Leu Leu Ala Gln Ala Lys Lys Leu Asp
        35                  40                  45

Asp Ala Gln
    50

<210> SEQ ID NO 5
<211> LENGTH: 51
<212> TYPE: PRT
<213> ORGANISM: Artificial Sequence
<220> FEATURE:
<223> OTHER INFORMATION: IgG Fc-binding polypeptide

<400> SEQUENCE: 5

Phe Trp Lys Glu Gln Gln His Ala Phe Tyr Glu Ile Leu His Leu Pro
1               5                   10                  15

Asn Leu Thr Glu Asp Gln Arg Gln Ala Phe Ile Ala Ser Leu Arg Lys
            20                  25                  30

Asp Pro Ser Gln Ser Ala Arg Leu Leu Ala Gly Ala Lys Lys Leu Asp
        35                  40                  45

Asp Ala Gln
    50

<210> SEQ ID NO 6
<211> LENGTH: 51
<212> TYPE: PRT
<213> ORGANISM: Artificial Sequence
<220> FEATURE:
<223> OTHER INFORMATION: IgG Fc-binding polypeptide

<400> SEQUENCE: 6

Phe Trp Lys Glu Gln Gln His Ala Phe Tyr Glu Ile Leu His Leu Pro
1               5                   10                  15

Asn Leu Thr Glu Gly Gln Lys His Ala Phe Ile Arg Ala Leu Arg Gly
            20                  25                  30

Asp Pro Ser Gln Ser Ala Arg Leu Leu Ala Arg Ala Lys Lys Leu Asp
        35                  40                  45

Asp Ala Gln
    50

<210> SEQ ID NO 7
<211> LENGTH: 58
<212> TYPE: PRT
<213> ORGANISM: Artificial Sequence
<220> FEATURE:
<223> OTHER INFORMATION: IgG Fc-binding polypeptide

<400> SEQUENCE: 7

Val Asp Ala Lys Phe Trp Lys Glu Gln Gln Asn Ala Phe Tyr Glu Ile
1               5                   10                  15

Leu His Leu Pro Asn Leu Thr Glu Asp Gln Arg His Ala Phe Ile Gly
            20                  25                  30

Thr Leu Arg Ala Asp Pro Ser Gln Ser Ala Arg Leu Leu Ala Gln Ala
        35                  40                  45

Lys Lys Leu Asp Asp Ala Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: IgG Fc-binding polypeptide

<400> SEQUENCE: 8

Val Asp Ala Lys Phe Trp Lys Glu Gln Gln His Ala Phe Tyr Glu Ile
1               5                   10                  15

Leu His Leu Pro Asn Leu Thr Glu Asp Gln Arg Gln Ala Phe Ile Ala
            20                  25                  30

Ser Leu Arg Lys Asp Pro Ser Gln Ser Ala Arg Leu Leu Ala Gly Ala
        35                  40                  45

Lys Lys Leu Asp Asp Ala Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: IgG Fc-binding polypeptide

<400> SEQUENCE: 9

Val Asp Ala Lys Phe Trp Lys Glu Gln Gln His Ala Phe Tyr Glu Ile
1               5                   10                  15

Leu His Leu Pro Asn Leu Thr Glu Gly Gln Lys His Ala Phe Ile Arg
            20                  25                  30

Ala Leu Arg Gly Asp Pro Ser Gln Ser Ala Arg Leu Leu Ala Arg Ala
        35                  40                  45

Lys Lys Leu Asp Asp Ala Gln Ala Pro Lys
    50                  55

<210> SEQ ID NO 10
<211> LENGTH: 58
<212> TYPE: PRT
<213> ORGANISM: Artificial Sequence
<220> FEATURE:
<223> OTHER INFORMATION: IgG Fc-binding polypeptide

<400> SEQUENCE: 10

```
Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Artificial Sequence
<220> FEATURE:
<223> OTHER INFORMATION: IgG Fc-binding polypeptide

<400> SEQUENCE: 11

Val Asp Asn Lys Phe Asn Lys Glu Gln Gln Ser Ala Phe Tyr Glu Ile
1               5                   10                  15

Leu His Leu Pro Asn Leu Asn Glu Gly Gln Glu His Ala Phe Ile Asn
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 12
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (4)..(4)
<223> OTHER INFORMATION: X is selected from H and N
<220> FEATURE:
<221> NAME/KEY: MISC_FEATURE
<222> LOCATION: (18)..(18)
<223> OTHER INFORMATION: X is selected from D and G
<220> FEATURE:
<221> NAME/KEY: MISC_FEATURE
<222> LOCATION: (20)..(20)
<223> OTHER INFORMATION: X is selected from R and K
<220> FEATURE:
<221> NAME/KEY: MISC_FEATURE
<222> LOCATION: (21)..(21)
<223> OTHER INFORMATION: X is selected from H and Q
<220> FEATURE:
<221> NAME/KEY: MISC_FEATURE
<222> LOCATION: (25)..(25)
<223> OTHER INFORMATION: X is selected from R, A and G
<220> FEATURE:
<221> NAME/KEY: MISC_FEATURE
<222> LOCATION: (26)..(26)
<223> OTHER INFORMATION: X is selected from A, S and T
<220> FEATURE:
<221> NAME/KEY: MISC_FEATURE
<222> LOCATION: (29)..(29)
<223> OTHER INFORMATION: X is selected from G, K and A

<400> SEQUENCE: 12

Glu Gln Gln Xaa Ala Phe Tyr Glu Ile Leu His Leu Pro Asn Leu Thr
1               5                   10                  15

Glu Xaa Gln Xaa Xaa Ala Phe Ile Xaa Xaa Leu Arg Xaa
            20                  25
```

<210> SEQ ID NO 13
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: Binding Motif within domain A of staphylococcal
      protein A

<400> SEQUENCE: 13

Ala Asp Asn Asn Phe Asn Lys Asp Pro Ser Gln Ser Ala Asn Leu Leu
1               5                   10                  15

Ser Glu Ala Lys Lys Leu Asn Glu Ser Gln Ala Pro Lys
            20                  25

<210> SEQ ID NO 14
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: Binding Motif within domain B of staphylococcal
      protein A

<400> SEQUENCE: 14

Ala Asp Asn Lys Phe Asn Lys Asp Pro Ser Gln Ser Ala Asn Leu Leu
1               5                   10                  15

Ala Glu Ala Lys Lys Leu Asn Asp Ala Gln Ala Pro Lys
            20                  25

<210> SEQ ID NO 15
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: Binding Motif within domain C of staphylococcal
      protein A

<400> SEQUENCE: 15

Ala Asp Asn Lys Phe Asn Lys Asp Pro Ser Val Ser Lys Glu Ile Leu
1               5                   10                  15

Ala Glu Ala Lys Lys Leu Asn Asp Ala Gln Ala Pro Lys
            20                  25

<210> SEQ ID NO 16
<211> LENGTH: 32
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (10)..(11)
<223> OTHER INFORMATION: Binding Motif within domain D of staphylococcal
      protein A

<400> SEQUENCE: 16

Ala Asp Ala Gln Gln Asn Asn Phe Asn Lys Asp Pro Ser Gln Ser Thr

```
                1               5                  10                  15
Asn Val Leu Gly Glu Ala Lys Lys Leu Asn Glu Ser Gln Ala Pro Lys
                    20                  25                  30

<210> SEQ ID NO 17
<211> LENGTH: 27
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (5)..(6)
<223> OTHER INFORMATION: Binding Motif within domain E of staphylococcal
      protein A

<400> SEQUENCE: 17

Ala Gln His Asp Glu Asp Pro Ser Gln Ser Ala Asn Cys Leu Gly Glu
1               5                   10                  15

Ala Gln Lys Leu Asn Asp Ser Gln Ala Pro Lys
            20                  25

<210> SEQ ID NO 18
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (7)..(8)
<223> OTHER INFORMATION: Binding Motif within the protein Z derivative
      of domain B of staphylococcal protein A

<400> SEQUENCE: 18

Val Asp Asn Lys Phe Asn Lys Asp Pro Ser Gln Ser Ala Asn Leu Leu
1               5                   10                  15

Ala Glu Ala Lys Lys Leu Asn Asp Ala Gln Ala Pro Lys
            20                  25

<210> SEQ ID NO 19
<211> LENGTH: 21
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (3)..(4)
<223> OTHER INFORMATION: Binding Motif is an IgG Fc-Binding Motif
<220> FEATURE:
<221> NAME/KEY: MISC_FEATURE
<222> LOCATION: (14)..(14)
<223> OTHER INFORMATION: Xaa is selected from R, G and Q

<400> SEQUENCE: 19

Phe Trp Lys Asp Pro Ser Gln Ser Ala Arg Leu Leu Ala Xaa Ala Lys
1               5                   10                  15

Lys Leu Asp Asp Gln
            20

<210> SEQ ID NO 20
<211> LENGTH: 28
<212> TYPE: PRT
<213> ORGANISM: Artificial Sequence
<220> FEATURE:
<223> OTHER INFORMATION: Engineered Polypeptide
<220> FEATURE:
```

```
<221> NAME/KEY: MISC_FEATURE
<222> LOCATION: (7)..(8)
<223> OTHER INFORMATION: Binding Motif is an IgG Fc-binding motif
<220> FEATURE:
<221> NAME/KEY: MISC_FEATURE
<222> LOCATION: (18)..(18)
<223> OTHER INFORMATION: Xaa is selected from R, G and Q

<400> SEQUENCE: 20

Val Asp Ala Lys Phe Trp Lys Asp Pro Ser Gln Ser Ala Arg Leu Leu
1               5                   10                  15

Ala Xaa Ala Lys Lys Leu Asp Asp Gln Ala Pro Lys
            20                  25

<210> SEQ ID NO 21
<211> LENGTH: 24
<212> TYPE: DNA
<213> ORGANISM: Artificial Sequence
<220> FEATURE:
<223> OTHER INFORMATION: Affibody Fragment

<400> SEQUENCE: 21
tgcttccggc tcgtatgttg tgtg                                          24

<210> SEQ ID NO 22
<211> LENGTH: 21
<212> TYPE: DNA
<213> ORGANISM: Artificial Sequence
<220> FEATURE:
<223> OTHER INFORMATION: Affibody Fragment

<400> SEQUENCE: 22
cggaaccaga gccaccaccg g                                             21

<210> SEQ ID NO 23
<211> LENGTH: 21
<212> TYPE: DNA
<213> ORGANISM: Artificial Sequence
<220> FEATURE:
<223> OTHER INFORMATION: Affibody Fragment
<220> FEATURE:
<221> NAME/KEY: misc_feature
<222> LOCATION: (1)..(1)
<223> OTHER INFORMATION: Biotin

<400> SEQUENCE: 23
cggaaccaga gccaccaccg g                                             21
```